United States Patent
Solie

(10) Patent No.: US 11,826,120 B1
(45) Date of Patent: Nov. 28, 2023

(54) METHOD FOR UTILIZING AN INTEGRATED WEIGHT SYSTEM IN A MEDICAL SERVICE KIOSK

(71) Applicant: MD Health RX Solutions, LLC, Tampa, FL (US)

(72) Inventor: Leonard Solie, Tampla, FL (US)

(73) Assignee: MD Health RX Solutions, LLC, Tampa, FL (US)

( * ) Notice: Subject to any disclaimer, the term of this patent is extended or adjusted under 35 U.S.C. 154(b) by 801 days.

(21) Appl. No.: 16/723,847

(22) Filed: Dec. 20, 2019

Related U.S. Application Data

(63) Continuation of application No. 16/692,775, filed on Nov. 22, 2019, which is a continuation-in-part of (Continued)

(51) Int. Cl.
*G16H 80/00* (2018.01)
*A61B 5/00* (2006.01)
(Continued)

(52) U.S. Cl.
CPC ............ *A61B 5/002* (2013.01); *A61B 5/0022* (2013.01); *A61B 5/4872* (2013.01); *A61B 5/742* (2013.01);
(Continued)

(58) Field of Classification Search
None
See application file for complete search history.

(56) References Cited

U.S. PATENT DOCUMENTS

| 5,012,348 A | 4/1991 | Witzel |
| 5,773,767 A | 6/1998 | Collins, Jr. |

(Continued)

FOREIGN PATENT DOCUMENTS

| WO | 02096339 A1 | 12/2002 |
| WO | 2014002091 | 1/2014 |

OTHER PUBLICATIONS

O'Heir, J. (2013). HealthSpot forms new partnerships, unveils telehealth kiosk. Dealerscope, 55(3), 14. Retrieved from https://dialog.proquest.com/professional/docview/1349217489?accountid=131444 (Year: 2013).*

(Continued)

*Primary Examiner* — Robert A Sorey
(74) *Attorney, Agent, or Firm* — PADDA LAW GROUP

(57) ABSTRACT

A medical services kiosk having an integrated weight scale assembly supporting private and secure telemedicine sessions between a patient and a remote network terminal utilized by a remote health care professional. The medical services kiosk comprising at least one privacy chamber having at least one door and a weight scale assembly. Each privacy chamber may include a user interactive display terminal that includes a display device, an input device, and a centralized processor, wherein the centralized processor is electronically communicable with the weight scale assembly. The weight scale assembly may comprise a housing, platform, processor, pressure blocks, and communication cables. In one exemplary form, the weight scale assembly may be able to calculate the patient's body mass index (BMI), body fat percentage, muscle mass, body water percentage, bone mass and the like.

20 Claims, 15 Drawing Sheets

Related U.S. Application Data application No. 16/573,756, filed on Sep. 17, 2019, which is a continuation-in-part of application No. 16/275,741, filed on Feb. 14, 2019, which is a continuation-in-part of application No. 13/777,864, filed on Feb. 26, 2013, now abandoned.

(60) Provisional application No. 61/606,095, filed on Mar. 2, 2012.

(51) Int. Cl.
*G16H 40/67* (2018.01)
*G16H 50/20* (2018.01)

(52) U.S. Cl.
CPC ............ *G16H 40/67* (2018.01); *G16H 50/20* (2018.01); *G16H 80/00* (2018.01)

(56) References Cited

U.S. PATENT DOCUMENTS

| | | | |
|---|---|---|---|
| 6,046,761 A | 4/2000 | Echerer | |
| 6,205,716 B1 | 3/2001 | Peltz | |
| 6,428,124 B1 | 8/2002 | Bluth et al. | |
| D501,557 S | 2/2005 | Collins et al. | |
| 7,445,600 B1 | 11/2008 | Carr et al. | |
| 7,912,733 B2 | 3/2011 | Clements et al. | |
| 7,986,369 B1* | 7/2011 | Burns .................... | F16M 11/40 396/428 |
| 9,723,273 B2* | 8/2017 | Child ............... | G08B 13/19626 |
| 10,052,026 B1* | 8/2018 | Tran ........................ | A61B 5/165 |
| 2002/0104271 A1 | 8/2002 | Gallant | |
| 2002/0172631 A1 | 11/2002 | Chandler, Jr. | |
| 2003/0178233 A1 | 9/2003 | Montagnino | |
| 2003/0216831 A1 | 11/2003 | Hart | |
| 2004/0044560 A1 | 3/2004 | Giglio et al. | |
| 2004/0090424 A1 | 5/2004 | Hurley | |
| 2004/0145676 A1 | 7/2004 | Lin | |
| 2005/0075907 A1 | 4/2005 | Rao | |
| 2005/0229834 A1 | 10/2005 | Wong | |
| 2005/0239037 A1 | 10/2005 | Ertsithichai | |
| 2006/0028717 A1 | 2/2006 | Dunn | |
| 2006/0106646 A1 | 5/2006 | Squilla et al. | |
| 2006/0143997 A1 | 7/2006 | Libenson | |
| 2006/0155589 A1 | 7/2006 | Lane | |
| 2006/0173267 A1 | 8/2006 | Chiang et al. | |
| 2006/0290885 A1 | 12/2006 | Covannon et al. | |
| 2007/0073113 A1 | 3/2007 | Squilla et al. | |
| 2007/0208241 A1 | 9/2007 | Drucker | |
| 2007/0212326 A1 | 9/2007 | Ochs | |
| 2008/0005974 A1 | 1/2008 | Delgado Vazquez | |
| 2009/0089085 A1 | 4/2009 | Schoenberg | |
| 2009/0137047 A1 | 5/2009 | Regan et al. | |
| 2009/0137882 A1 | 5/2009 | Baudino | |
| 2009/0160876 A1 | 6/2009 | King et al. | |
| 2009/0167531 A1 | 7/2009 | Ferguson | |
| 2009/0167838 A1 | 7/2009 | Poisner | |
| 2009/0233769 A1 | 9/2009 | Pryor | |
| 2009/0240527 A1 | 9/2009 | Bluth | |
| 2009/0241177 A1 | 9/2009 | Bluth | |
| 2009/0276242 A1 | 11/2009 | Waisbren | |
| 2010/0130873 A1 | 5/2010 | Yuen | |
| 2011/0015934 A1 | 1/2011 | Rowe | |
| 2011/0130635 A1 | 6/2011 | Ross | |
| 2011/0191123 A1 | 8/2011 | Buzynski | |
| 2011/0248818 A1 | 10/2011 | Peak | |
| 2011/0315611 A1 | 12/2011 | Fulkerson | |
| 2012/0179479 A1* | 7/2012 | Waterson ............... | G16H 80/00 705/2 |
| 2012/0253837 A1* | 10/2012 | Cashman .............. | E04H 1/1205 705/2 |
| 2012/0275167 A1 | 11/2012 | Scruggs | |
| 2012/0289850 A1 | 11/2012 | Xu | |
| 2013/0014985 A1 | 1/2013 | Ferrara | |
| 2013/0062127 A1 | 3/2013 | Pangrazio | |
| 2013/0172787 A1* | 7/2013 | Marovets ............. | A61B 5/1072 600/587 |
| 2013/0186429 A1 | 7/2013 | Morita | |
| 2013/0297219 A1 | 11/2013 | Bangera | |
| 2014/0095196 A1 | 4/2014 | Waterson | |
| 2014/0139616 A1 | 5/2014 | Pinter | |
| 2015/0042822 A1 | 2/2015 | Le | |
| 2016/0105641 A1 | 4/2016 | Periyannan | |
| 2017/0323070 A1 | 11/2017 | Hodge | |
| 2018/0192965 A1 | 7/2018 | Rose | |
| 2018/0328780 A1* | 11/2018 | Cochran .............. | A61B 6/4283 |
| 2021/0035400 A1 | 2/2021 | Flynn | |
| 2022/0277608 A1 | 9/2022 | Brandauer | |

OTHER PUBLICATIONS

Screen shot of Internet web site http://bigthink.com—Teaches virtual doctor in a kiosk Link: http://bigthink.com/ideas/40455?page=all.

Screen shot of Internet web site www.emrandehr.com—Teaches virtual doctor in a kiosk Link: http://www.emrandehr.com/2011/10/03/virtual-doc-kiosks-a-giant-leap-for-telehealth/.

Screen shot of Internet web site www.fastcompany.com http://www.fastcompany.com/magazine/155/the-virtual-doctor-will-see-you-now.html.

Screen shot of Internet web site www.medlegalsource.com—teaches a combined medical/legal consulting website Link: http://www.medlegalsource.com/terms-of-use.

\* cited by examiner

METHOD FOR UTILIZING AN INTEGRATED WEIGHT SYSTEM IN A MEDICAL SERVICE KIOSK

CROSS-REFERENCE TO RELATED APPLICATIONS

This U.S. nonprovisional patent application is a continuation of U.S. nonprovisional patent application Ser. No. 16/692,775, filed on Nov. 22, 2019, which is a continuation-in-part application of U.S. nonprovisional patent application Ser. No. 16/573,756, filed on Sep. 17, 2019, which claims the benefit of U.S. nonprovisional patent application Ser. No. 16/275,741, filed on Feb. 14, 2019, which claims the benefit of U.S. nonprovisional patent application Ser. No. 13/777,864, filed on Feb. 26, 2013, which, in-turn, claims the benefit of U.S. provisional patent application Ser. No. 61/606,095, filed on Mar. 2, 2012 U.S. nonprovisional application Ser. No. 16/573,756, U.S. nonprovisional patent application Ser. No. 16/275,741, U.S. nonprovisional patent application Ser. No. 13/777,864, and U.S. provisional patent application Ser. No. 61/606,095 are incorporated-by-reference herein in their entirety.

FIELD OF THE INVENTION

The present invention relates generally to a medical kiosk, and more particularly, to a medical kiosk or booth that includes an integrated weight scale system that may be used by a patient to obtain a weight measurement during a medical session with a remote physician who is remotely connected supervising the session.

BACKGROUND OF THE INVENTION

Medical care is a need for every individual and every family. Many individuals have one or more physicians or other medical professionals that they see for wellness visits and for treatment of various illnesses and injuries. However, as the population continues to grow and healthcare continues to evolve, the need for doctors and health care providers continues to grow as well. As a result of this growth, medical facilities such as hospitals and doctors' offices are operating at maximum physical capacity. Since the population continues to grow and the need for doctors and health care providers is not expected to abate in the near or immediate future, there is a need for an alternative more efficient manner to see patients rather than physically seeing them on-site.

Medical facilities in general have been attempting to improve efficiency through utilizing technology. In particular, some aspects of patient care have been computerized through the use of electronic terminals interactively accessible to the patients. Currently, processes such as checking in and prescription refill requests may be handled entirely by digital mediums. These digital mediums may be in the form of specialized hardware and software for collecting, organizing, and updating information associated with patients.

Hospitals and medical clinics recently began utilizing interactive devices that allow patients to perform routine activities. The ability for patients to perform operations such as update personal information linked to their health profile, pay medical fees, and other various routine activities via these interactive devices has generated a significant increase in efficiency for medical facilities. However, patients are still required to be physically on-site in order for medical professionals to perform routine medical activities that are necessary to treat a patient such as measuring vital signs.

There have also been limitations regarding doctor and medical professional availability in the case when an individual requires immediate attention. For example, if an individual were to decide to visit a doctor or medical professional's office for a non-emergency the day of, then that individual would be classified as a "walk-in" if he or she did not have an appointment and would be subjected to a wait time associated with the current workload of the medical facility. The individual's only alternative would be to go the emergency room of a hospital for a non-emergency matter.

Recently, there have been developments in implementations of various systems and methods relating to telehealth and telemedicine. However, these systems and methods require a substantial amount of improvement in order for them to be nearly as efficient as the conventional practice of medicine.

Thus, there is a need for a medical services system that allows doctors and other medical professionals to examine, diagnose, and treat patients without requiring the patients to be physically present with the medical professional.

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section.

SUMMARY OF THE INVENTION

The present invention is directed to a medical services kiosk that is capable of generating a plurality of interactions between a user or patient and one or more medical professionals via a network comprising a plurality of client devices. The medical services kiosk further comprises a patient station that satisfies the need for providing facilities for remote interaction with health care professionals in real time. The medical services kiosk is configured to support examination, diagnosis, and treatment of a patient via establishing a tele-communicative connection between the patient and remote medical professionals via the network.

Introducing a first embodiment of the invention a medical services kiosk with an integrated weight scale mechanism, comprising:
- a unit defining an interior space having a closed top, a closed bottom, a pair of opposite right and left sides, a front end, and a back end;
- at least one patient station provided inside of said interior space of said unit, the at least one patient station comprising:
- a privacy chamber formed by at least four upstanding side walls affixed to a flooring and having at least one door, wherein the privacy chamber is provided for receiving a patient therein and allowing the patient to have a medical session over a network with a remote health care professional;
- an electronic device, wherein the electronic device is electronically communicable over the network with a cloud based system and a remotely located network terminal accessible by the remote health care professional, wherein the medical session is hosted by said cloud based system; and
- a weight scale assembly, wherein the weight scale assembly is communicable with the electronic device.

In another aspect, the flooring of the privacy chamber may include a floor cavity.

In yet another aspect, the weight scale assembly may comprise a housing formed by at least four upstanding side walls affixed to a base defining a hollow interior, and a platform of a planar configuration having at least four sides providing a top end and a bottom end, wherein the platform is securable to a top of said housing.

In another aspect, the weight scale assembly may further comprise a processor, at least four sensor blocks, a communication cable, a mounting bracket, and a transmitting cable.

In another aspect, the mounting bracket may comprise a planar plate of a thickness having a plurality of fasteners holes on an end of the planar plate and a mounting platform for receiving a respective one of the at least four sensor blocks on an opposite end of the planar plate.

In another aspect, the network may include any one of a wired, a wireless, and an internet network.

In yet another aspect, the patient station may include antimicrobial surfaces.

Introducing a method for providing a remote real time patient aliment diagnoses and treatment, the method including the steps of:

A method for using a weight scale assembly in a medical services kiosk that provides remote real time readings, said method including the steps of:
- (a) receiving a patient within a patient station, said patient station comprising:
  - a privacy chamber formed by at least four upstanding side walls affixed to a flooring having a floor cavity and including at least one door, wherein said privacy chamber is provided for receiving a patient therein and allowing said patient to have a medical session over a network with a remote health care professional;
  - an electronic device, wherein said electronic device is electronically communicable over said network with a cloud based system and a remotely located network terminal accessible by said remote health care professional, wherein said medical session is hosted by said cloud based system;
  - a weight scale assembly integratable with said floor cavity of said privacy chamber, comprising,
    - a housing formed by at least four upstanding side walls affixed to a base defining a hollow interior,
    - a platform of a planar configuration having at least four sides providing a top end and a bottom end, wherein said platform is securable to a top of said housing,
    - a processor disposed within said hollow interior,
    - a plurality of sensor blocks disposed within said hollow interior,
    - a mounting bracket coupled to each one of said plurality of sensor blocks and affixed to said base of said housing,
    - a communication cable connected to each one of said plurality of sensor blocks connecting said plurality of sensor blocks to said processor, and
    - a transmitting communication cable, wherein said transmitting communication cable stems from said processor and is connected to said electronic device;
- (b) sending instructions from said electronic device to said cloud based system that said patient is initiating a medical session;
- (c) establishing a connection between said electronic device and said remotely located network terminal over said network, wherein said remotely located network terminal is accessible by a healthcare professional;
- (d) enabling bi-directional communication between said patient and said healthcare professional;
- (e) requiring that said patient step on said platform of said weight scale assembly;
- (f) transmitting data being produced by said sensor blocks to said processor by way of said communication cable;
- (g) transmitting said data from said processor to said electronic device by way of said transmitting communication cable;
- (h) establishing a measurement reading;
- (i) displaying said measurement reading on a display device of said electronic device, wherein said measurement reading being displayed on said display device is a body weight reading presented in numerical form;
- (j) terminating said medical session; and
- (k) activating a purification system included inside of said privacy chamber after said patient has terminated said session and has left said privacy chamber, wherein said purification system includes an ultraviolet light device.

As described herein, medical professional may include but is not limited to any doctor, pharmacist, nurse practitioner, nurse, nursing assistant, or any other individual who examines and treats or assists in the examination and treatment of patients for medical purposes.

These and other objects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which:

FIG. 5 presents a cut-out view of the medical service kiosk shown in FIG. 2, illustrating a few of the medical equipment that the medical service kiosk is equipped with;

Like reference numerals refer to like parts throughout the several views of the drawings.

DETAILED DESCRIPTION

In the following description, for the purposes of explanation, numerous specific details are set forth in order to provide a thorough understanding of the present invention. It will be apparent, however, that the present invention may be practiced without these specific details, In other instances, well-known structures and devices are shown in block diagram form in order to avoid unnecessarily obscuring the present invention. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Figure 1:
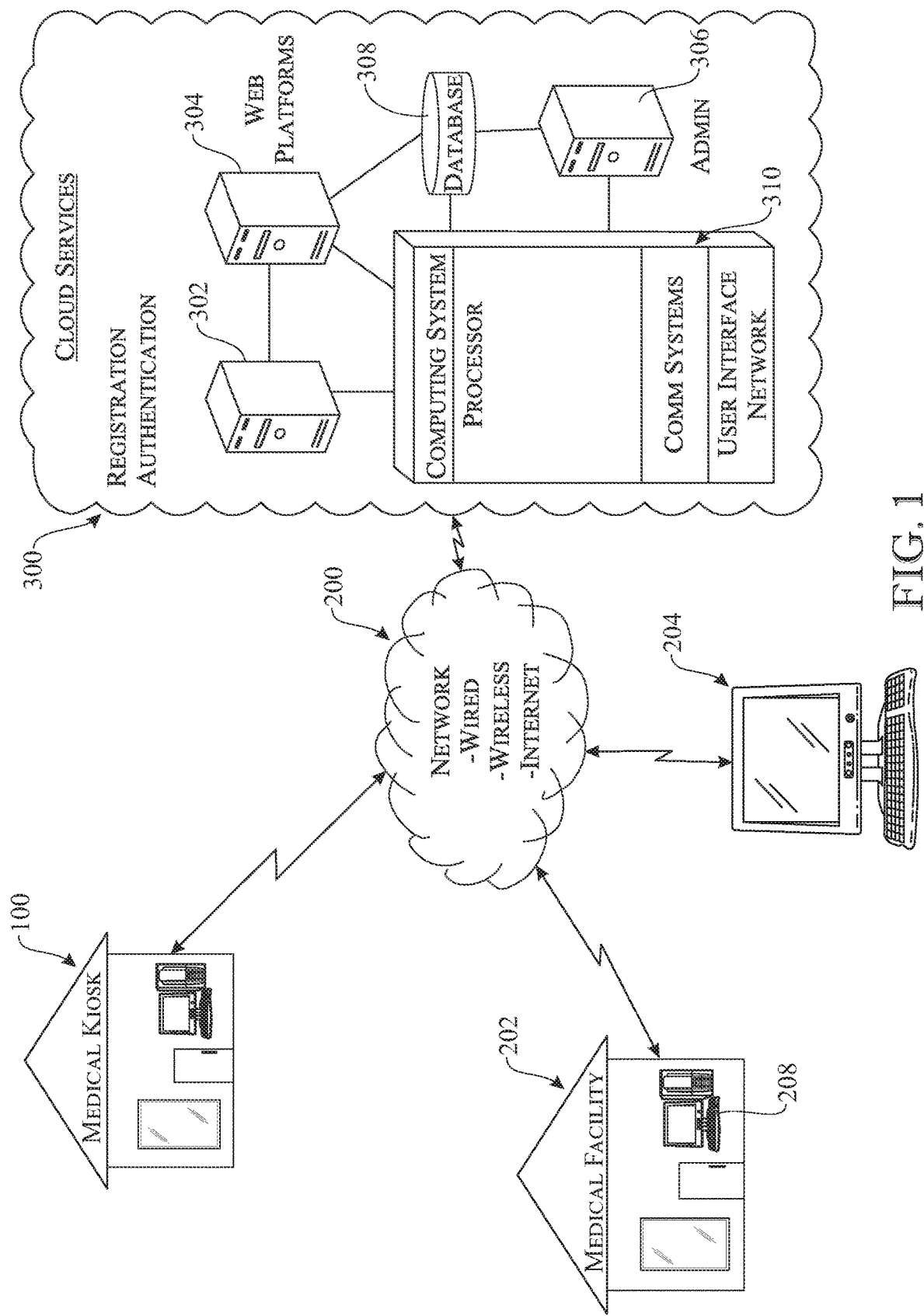
FIG. 1 presents a schematic view of a medical service kiosk communicatively coupled to a medical facility located remotely thereof, both the medical service kiosk and medical facility communicatively coupled to a cloud based server via a network.

Initially referring to FIG. 1 there is shown a schematic view of a remote real time medical assistance system, showing a medical service kiosk 100, and a medical facility 202 in bidirectional communication and hosted on a cloud services system 300 over an accessible communication network 200, in accordance with an embodiment of the present invention. It is appreciated that any number of medical service kiosks 100 and medical facilities 202, which can include one or more terminals, computers or servers, can access and use the cloud services system 300. As illustrated in FIG. 1, the medical service kiosk 100 and medical facility 202 communicates with the cloud services system 300 via a wired, wireless, or internet connection network 200. The medical service kiosk 100 gives access to at least one patient to a secure medical session with a physician or healthcare professional that is located at the remote medical facility 202, or on a remote electronic device 204 at a remote location, such as their office, home, or an alternative remote location over the network terminal 200. Patient access to the medical session with a physician at a medical facility 202 hosted by the cloud services system 300, is accomplished by use of an electronic device including any of, but not limited to, a tablet, laptop or notebook computer, or a desktop computer. It is appreciated that each medical session may be recorded and stored in memory or a database 308 provided by the cloud services system 300 for later viewing. In application, each electronic device includes the necessary electronic components required to communicate with the medical facility 202, and cloud services system 300. As such, each patient electronic device may include audio and video circuitry, a keyboard or touchpad, memory or access to memory, one or more processors, I/O network interface, application program interface, read/write memory (RAM), read-only memory (ROM), and a visual screen or display for navigating through a medical session hosted on the cloud services system 300.

Each electronic device utilized to connect to the cloud services system 300, hosting the medical session, electrically communicates via a wired (land line), wireless, or internet network including VOIP (voice over internet protocol) network. The communication network 200 may include wireless communication including but not limited to: WLAN (wireless local area network, Wi-Fi (IEEE 802.11), WPANS (wireless personal area networks, such as Bluetooth (IEEE 802.15), Infrared, ZigBee), WMAN (wireless metropolitan area network, such as WiMax (II-EE 802.16)), WWAN (wireless wide area networks, internet), and GAN (global area network), a mobile wireless communication system, such as 3G, 4G, or 5G, an internet-protocol based communication system. The communication network 200 may include a wired communication including but not limited to, fiber optic systems, a telephone network such as a PSTN (public standard telephone network). The communication network 200 may further include a radio frequency network (RF), a cable network, a satellite network, and an internet or intranet network, where each network is adapted for transmitting, and receiving data, information, audio, video, texts, messages, emails, and files between the medical kiosk electronic devices and the medical facility 202, and cloud services system 300. It will be noted that network, interface, communication and information exchange equipment, components or peripherals may be employed, including, but not limited to, use of base stations, servers, routers, switches, repeaters, towers, antennas, Ethernet hubs, wired or wireless data pathways, modems, virtual private networks (VPN), modems, proxy servers, application program interfaces (APIs), networking adapters, or gateways. Encryption protocols may also be employed to secure the transmitted information, data, or messages. For example, a few exemplary forms of encryption include IPsec, or secure sockets layer (SSL), and symmetric or asymmetric encryption.

The cloud service system 300 comprises an internet based computing service system including in one embodiment, a user registration/authentication server 302, a web platform server 304, and an administrative server 306, all networked together by way of a central database 308, and computing system 310. The cloud service system 300 may include a public, private, or hybrid cloud configuration based on various cloud service models including any of an Iaas (Infrastructure as a Service), PaaS (platform as a Service), or Saas (Software as a Service) model. The type of cloud configuration implemented is based on need for data security, control over the infrastructure, sensitivity of data and applications, and industry regulations or standards. In a preferred embodiment, the cloud computing services 300 comprises the Amazon Web Services (AWS) elastic compute cloud EC2 architecture that supports simple email service (SES), and simple notification service (SNS) to allow both email and short message service (SMS) communication between patients/medical care providers, and the AWS cloud computing services 300, via, electronic devices over network 200. The AWS cloud computing services 300 also supports simple storage service (a single web-services interface) to store and retrieve data from anywhere on the web.

With continued reference to FIG. 1, after establishing a secure connection with a health care professional over the communication network 200, which will be described further herein below, the patient will be able to communicate with the healthcare professional (e.g., clinician, physician, pharmacist, nurse practitioner, nurse, nursing assistant, etc.) and provide the healthcare professional with medical information through the use of equipment that is provided inside of the patient station 102 and is connected to the electronic device inside of the medical service kiosk 100. The health care professional or physician will be able to guide and instruct the patient on how to use the equipment provided therein. The equipment inside of the patient station is communicable with the central processor of the electronic device inside of the patient station, and can transfer readable data to the cloud services system 300, and the network terminal accessible 208 or electronic device 204 being used by the physician overseeing the medical session. The physician may review the information (i.e., readable data) that is being transmitted in real-time, and render a medical opinion. The health care professional will also be able to provide medicine that can be dispensed by the medical kiosk medical storage space provided by the medical services kiosk 100, or, alternatively, remotely print a prescription or send a prescription notification to a nearby pharmacy for pick-up. In one exemplary form, the medical services kiosk 100 may be connected to a back-up generator or to at least one uninterruptible power supply (UPS) battery that is powerful enough to energize the medical services kiosk, and particularly the equipment inside of each respective patient station in the event of an unexpected power loss.

Figure 2:
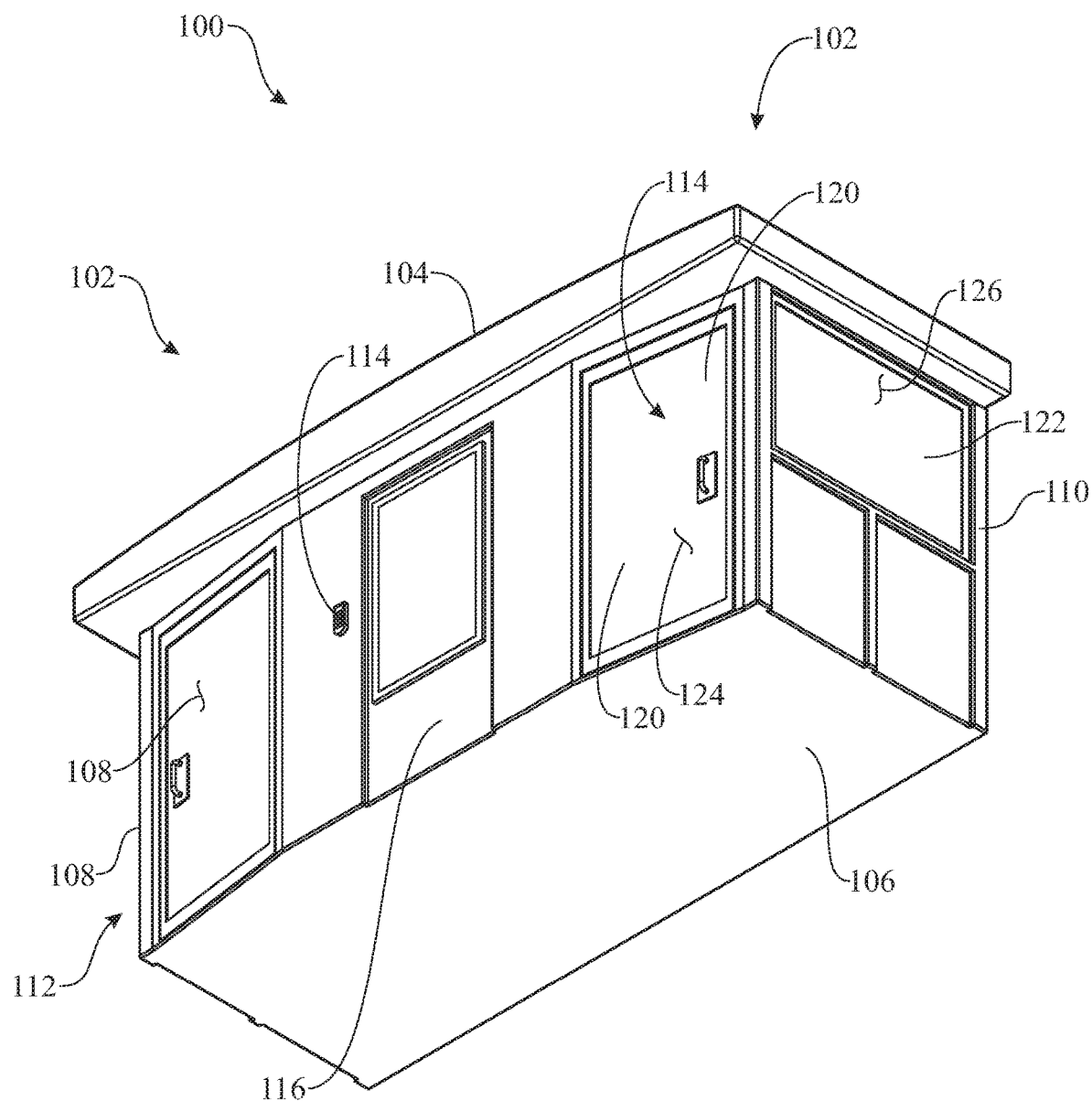
FIG. 2 presents a bottom isometric view of an exemplary embodiment of a medical service kiosk.
Figure 3:
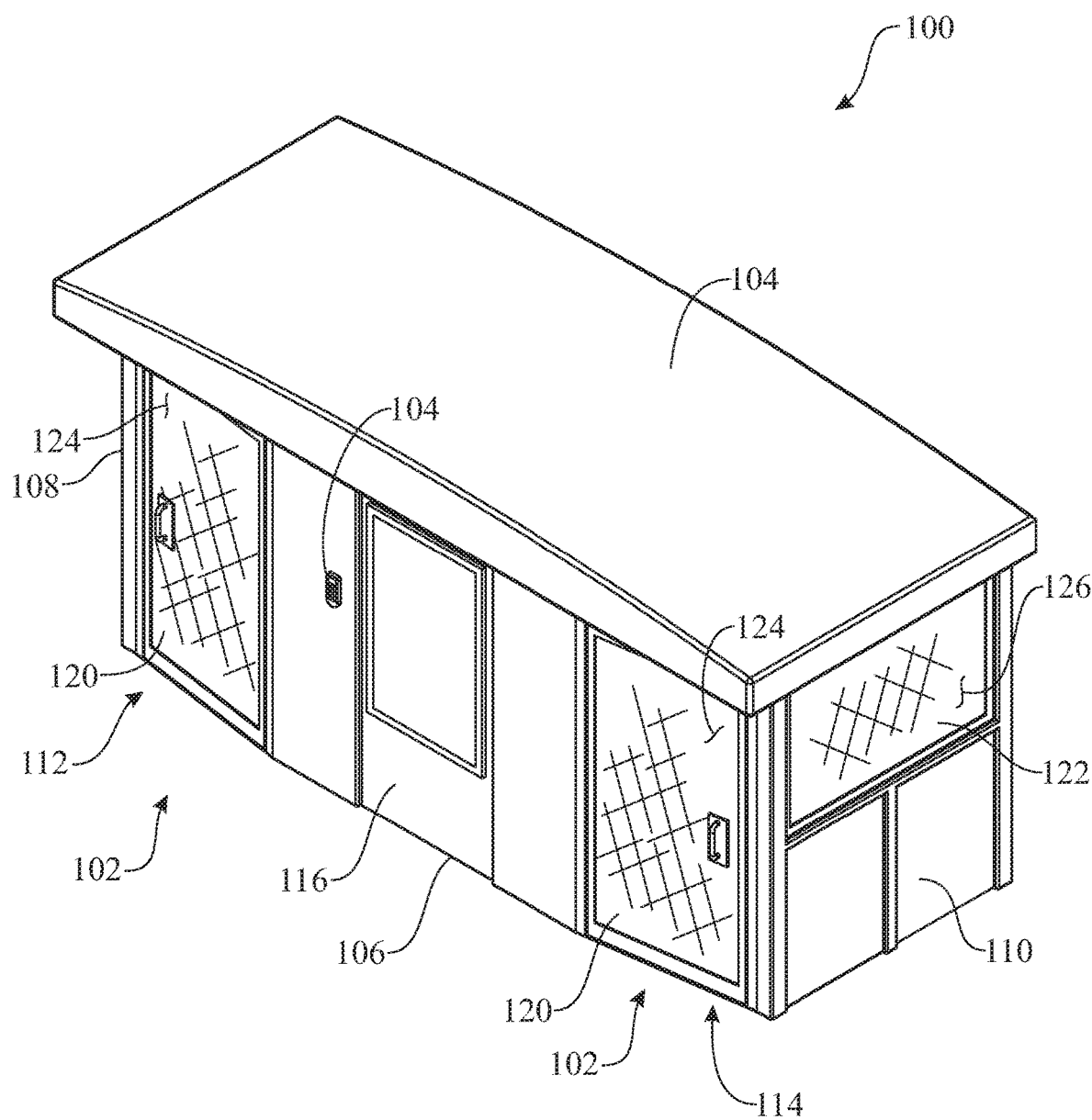
FIG. 3 presents a top isometric view of the medical service kiosk originally shown in FIG. 2, wherein the window and door panels include an automatic glass shading element that provide privacy to a patient when using the medical service kiosk.
Figure 4:
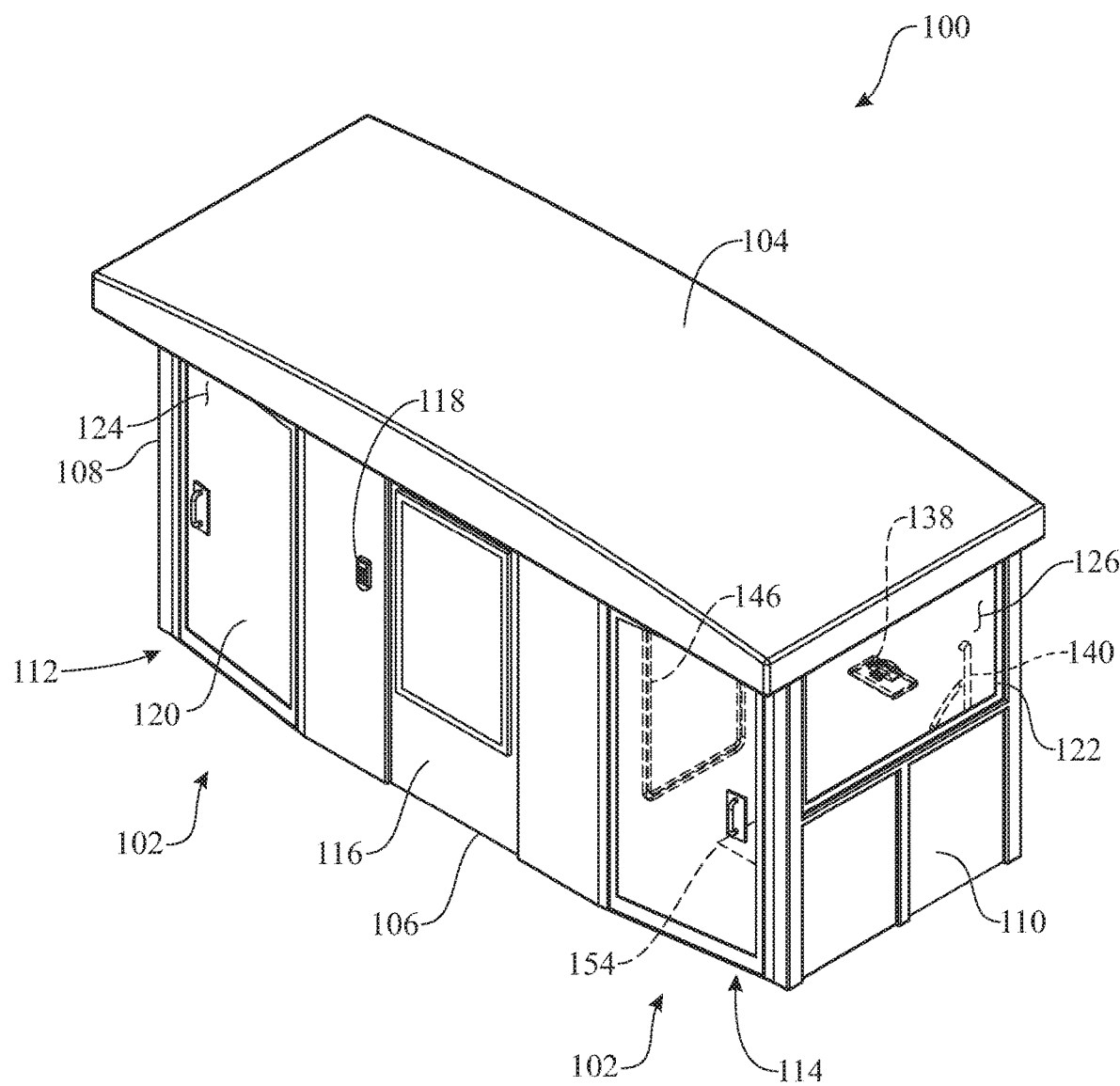
FIG. 4 presents a top isometric view of the medical service kiosk originally shown in FIG. 2, with the automatic glass shading element turned off and showing the interior of the patient station.

Referring now to FIGS. 2-4, the medical services kiosk 100 is illustrated in accordance with one exemplary embodiment of the present invention. The medical services kiosk 100 includes a closed top 104, a closed bottom 106, and opposite left 108 and right 110 sides. In this particular example, as mentioned heretofore, the medical kiosk 100 includes two patient stations 102, a leftmost patient station 112 and a rightmost patient station 114. It should be readily understood, however, that each medical services kiosk 100 may include at least one or more patient stations 102. Each medical services kiosk 100 may also include a medical inventory storage vault or space 116. The medical inventory storage space 116 may generally comprise a medical dispenser containing a plurality of medications securely locked therein and/or include medical equipment (e.g., over-the-counter blood pressure equipment, pregnancy tests, blood sugar monitors, etc.) that may be distributed to a patient upon a set of instructions and commands provided over the network by the medical professional (i.e., a physician) that is administering the exam remotely. The storage space 116 may be configured to include a security check device 118 that scans barcodes, RFID, prescriptions, and/or the like, before administering or giving access to the medication and equipment stored therein.

As specifically shown in FIGS. 3 and 4, the leftmost patient station 112 and rightmost patient station 114 each include an entrance door 120 and a side window panel 122 that may include a privacy feature governed by a privacy system. For instance, in one exemplary form, entrance door 120 and side window panel 122 may each be configured to include a privacy glass 124, 126 that includes polymer dispersed liquid crystals whose light scattering power is adjustable through the application of an electrical field. In their natural (i.e., uncharged) state, the liquid crystal molecules are randomly scattered providing an opaque condition that prevents anyone from peering through the glass 124, 126, giving the patient complete privacy (FIG. 3) When a current is applied (i.e., charged state), however, the molecules align to provide a see through condition, as shown in FIG. 4. It is also appreciated that the patient kiosk includes a display device projectable on the privacy glass of the entrance door that notifies other patient's outside of the interior chamber that the patient station is in use.

Figure 5:
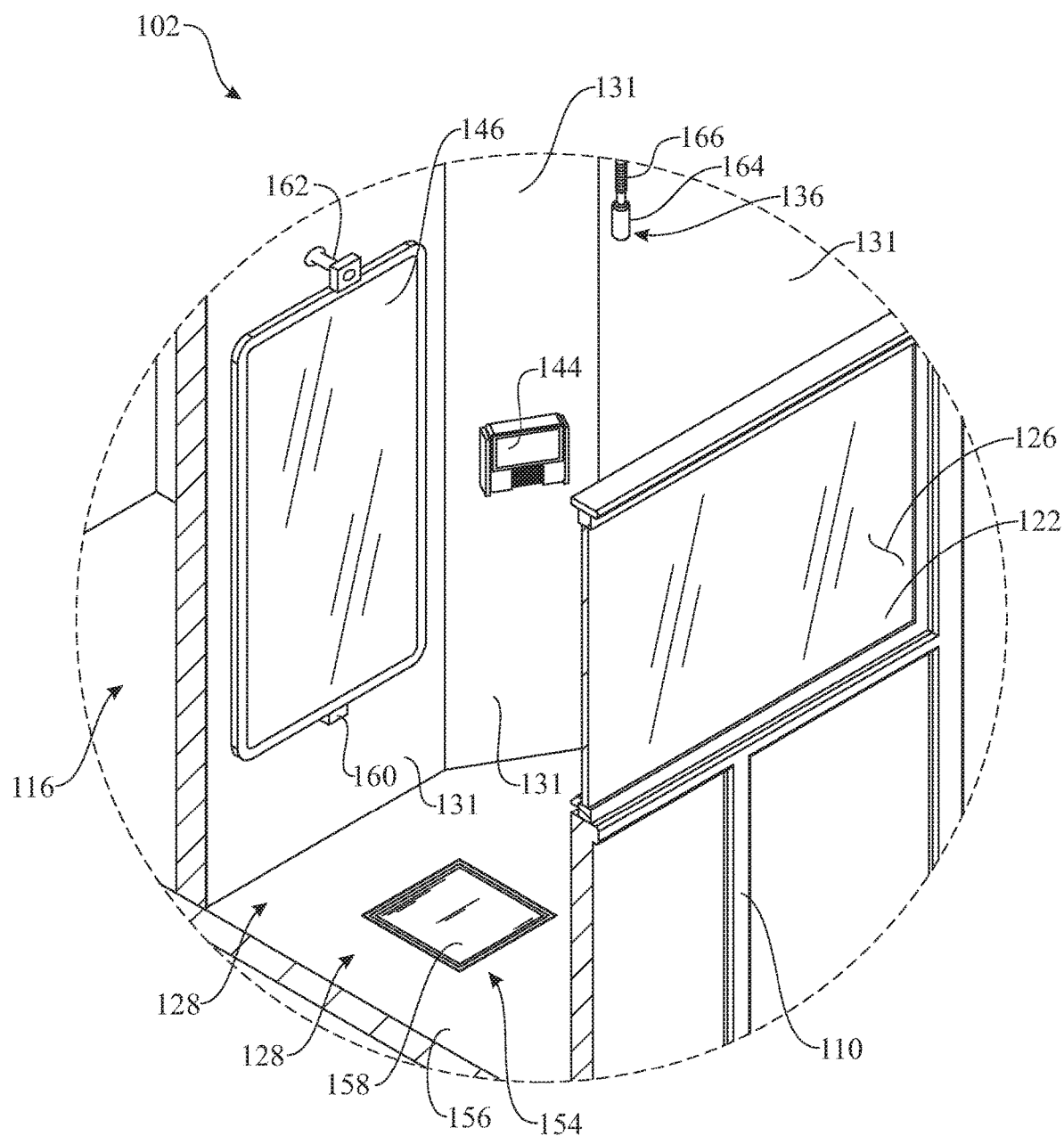
Figure 6:
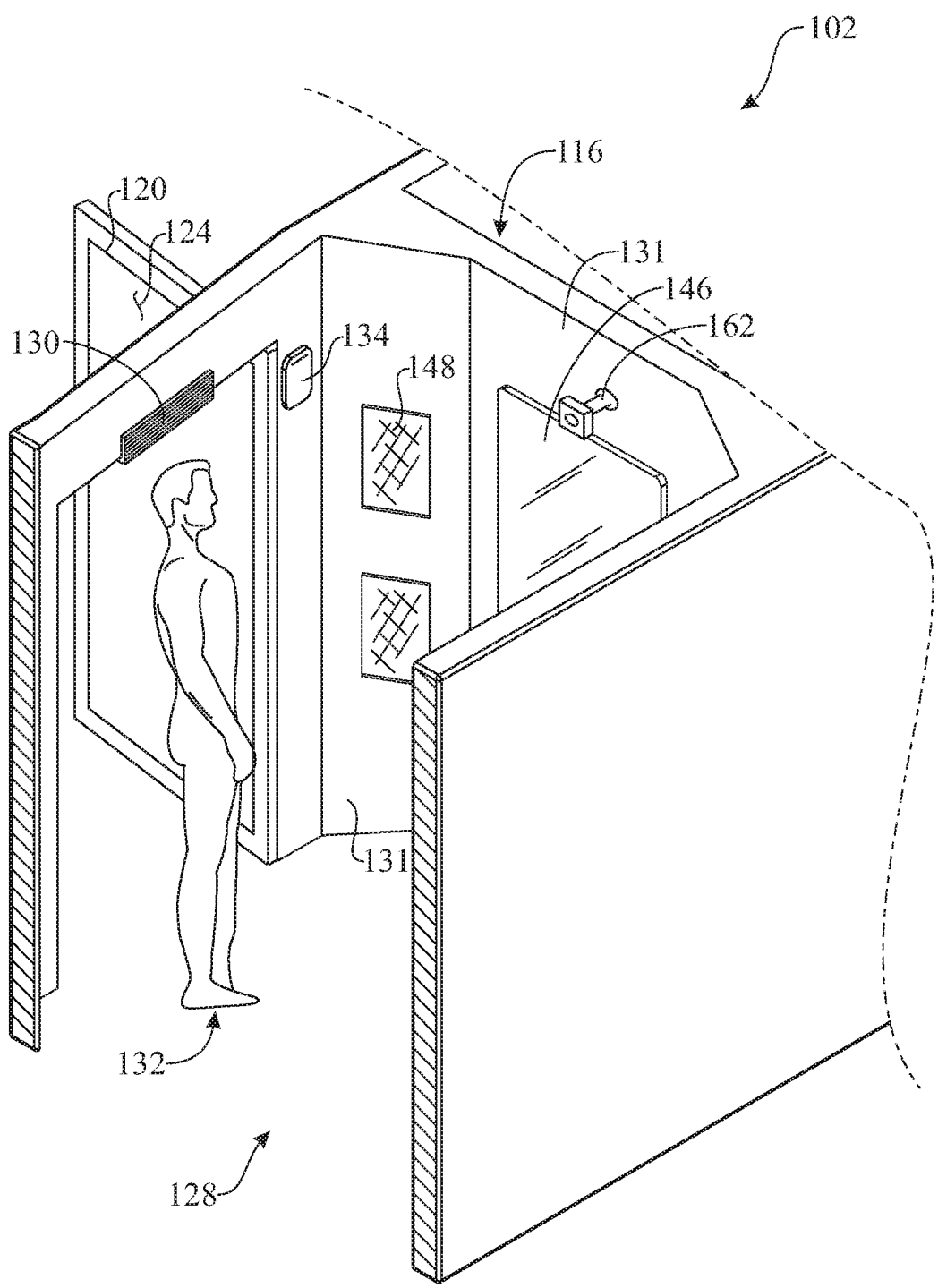
FIG. 6 presents another cut-out view of the medical service kiosk, showing a patient walking in to the patient station.

Turning now to FIGS. 4-6, as previously mentioned the medical service kiosk 100 may include more than one patient station 102. Although each patient station 102 may be provided to include certain medical equipment that another station may omit, a vast majority of patient stations 102 are contemplated to be made of a similar shape, size, and be equally equipped to provide a sense of familiarity to the visiting patient regardless of the location of the medical service kiosk being visited. Therefore, the following is a continued description of one exemplary patient station 102.

As is best seen in FIGS. 5 and 6, the patient station 102 generally includes an interior chamber 128 comprising a plurality of walls 131 that are sound proof. The patient station 102 may also include the aforementioned doorway or entrance door 120, which may include an automatic locking mechanism 130. The locking mechanism 130 is contemplated to be part of the privacy system that includes the aforementioned privacy feature on the glass 124, 126 of the entrance door 120 and window panel 122, which can be selectively switched from a see-through condition to an opaque condition and vice versa. It is appreciated that the privacy system be controlled by a power distribution unit (PDU) or control box 134, which may be located in the storage vault 116. The control box 134 in one exemplary embodiment is communicable with the electronic network 200, medical facility 202 and cloud service system 300 and hosts an executable set of instructions or commands. The control box 134, which is isolated from the patient station's electronic device centralized processor, may be connected to a network switch and may receive control commands that the station's centralized processor doesn't. Some control commands may be sent (i.e., executed) by the physician overseeing the medical session, or programmed to run automatically by pre-set programmed protocols. In one exemplary embodiment, control box 134 may be configured to automatically activate the privacy system after a patient 132 has initiated their session. For instance, after a patient 132 has walked into the interior chamber 128 of the patient station 102 and has successfully initiated their medical session as will be described herein below, the privacy system activates prompting the automatic locking mechanism 130 to engage and secure entrance door 120 to prevent entry into the patient station 102. At the same time, the privacy system activates the privacy feature on the entrance door's glass 124 and window glass 126 to prevent or obscure a sight line view into the interior chamber 128 of the patient station 102. Once the medical session is complete (i.e., the session has been terminated), the privacy system disengages deactivating the privacy feature on the door glass 124, window panel glass 126, and locking mechanism 130 to unlock the door 120. In one exemplary form, the automatic locking mechanism may be provided in the form of an electronic maglock. Alternative locking mechanisms, such as standard door locks, deadbolts, or other types electronic locks that are electronically communicable with an electronic device may be used. The activation and deactivation of the privacy system as described hereinabove, may be operated through firmware and software. It is also contemplated that the physician overseeing the medical session may have control over the activation and deactivation of the privacy system remotely through the terminal being used for the medical session.

Figure 7:
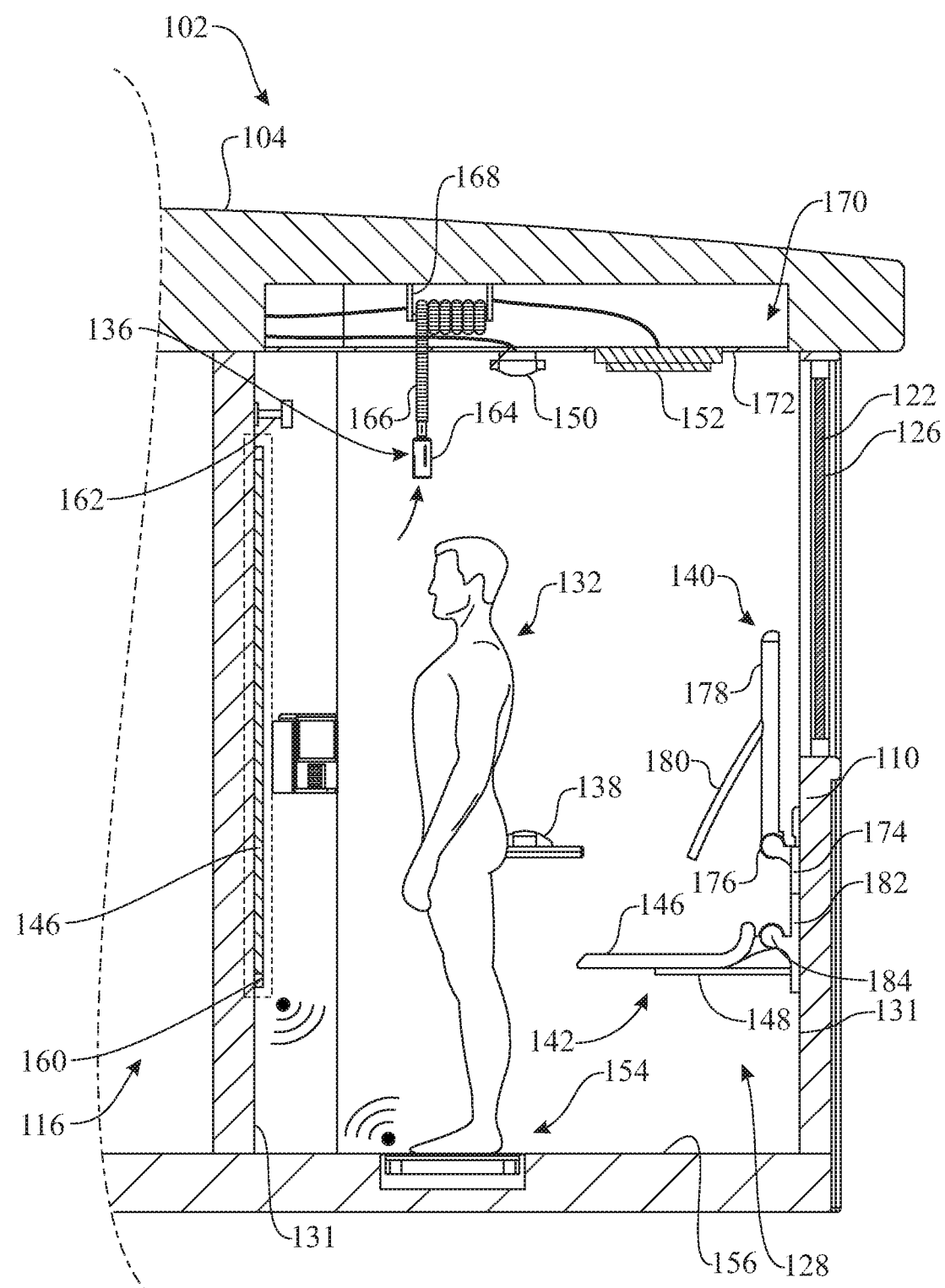
FIG. 7 presents a cross-sectional side elevation view of the medical service kiosk shown in FIG. 2, with the patient communicating with a physician before starting a physical examination.

Referring now to FIGS. 5-7 and 9, the patient station 102 may also include a number of medical and non-medical equipment. For example, as best shown in FIG. 7, the patient station 102 may include a retractable diagnostic camera device 136, a web camera or live-video capturing camera 162 positioned at a wall 131 above a visual device e.g., a screen) pointing in the general direction of a space that is to be occupied by the standing patient 132. The capturing camera 162 is able to transmit an image of the patient 132 occupying the patient station 102 to the physician 202 conducting the exam at the medical facility 202 (or to the physician on their electronic device 204 shown in FIG. 1). All cameras included in the patient station are communicable and connected to the user interactive display via a wired (e.g., USB connector) or wireless connection (e.g., Bluetooth, internet connection, radio wave frequency, etc.). Each patient station may also include a stethoscope that can be deployed and retracted in a similar fashion to the retractable diagnostic camera, and be mounted to either the ceiling or wall of the interior chamber.

The patient station 102 may also include a biometrical/vitals measuring device 138, an arm support mechanism 140, a seating mechanism 142, a documentation receiving device 144 (or card reader), the user interactive display terminal 146, which is the station's electronic device, may include speakers 148, a microphone 160, a monitor, screen, or projector. The patient station 102 may also include a purification device or ultra-violet sanitation system 150, an interior lighting mechanism 152, and an integrated scaling mechanism 154 comprising an outer flooring 156 and a platform or interior flooring 158. The interior chamber 128 may further comprise a plurality of stationary and retractable sensors, cameras, and other devices that are communicable over a wired and/or wireless network with the station's centralized processor. As illustrated best in FIG. 9, the retractable diagnostic camera device 136 may comprise a camera head 164 that may be configured to include means for measuring and receiving bodily conditions, as well as capturing images. For example, the diagnostic camera device 136 may include an interchangeable camera head 164 to include, but not limited to, a manual focusing head, an otoscope head, a tongue depressor attachment and derm hood head. The camera head may also include buttons that allow the patient to capture images upon the request of the physician overseeing the medical session. A separate camera may also be included to provide thermal images, thermal temperature readings, and color-coded imaging to the physician administering the remote medical session.

The position of the diagnostic camera device 136 may generally comprise a camera head 164 affixed to a camera cord 166 that is set about a linear mechanism 168. As is best illustrated, the linear mechanism 168 may be suspended inside of a cavity 170 provided by a false ceiling 172 inside of the interior chamber 128 of the patient station 102, or alternatively be positioned inside of the medical inventory storage space 116 of the patient station 102 (not shown). It is appreciated that the retractable camera device 136 be arranged or otherwise positioned at a top of the interior chamber 112, generally over a space that is to be occupied by the standing patient 132 and at a height that is easily accessible by the patient 132. In an alternative embodiment, the camera 164, camera cord 166, and linear mechanism 168 may be disposed about a wall surface 131 at a height that is equally accessible by the patient 132.

Figure 10:
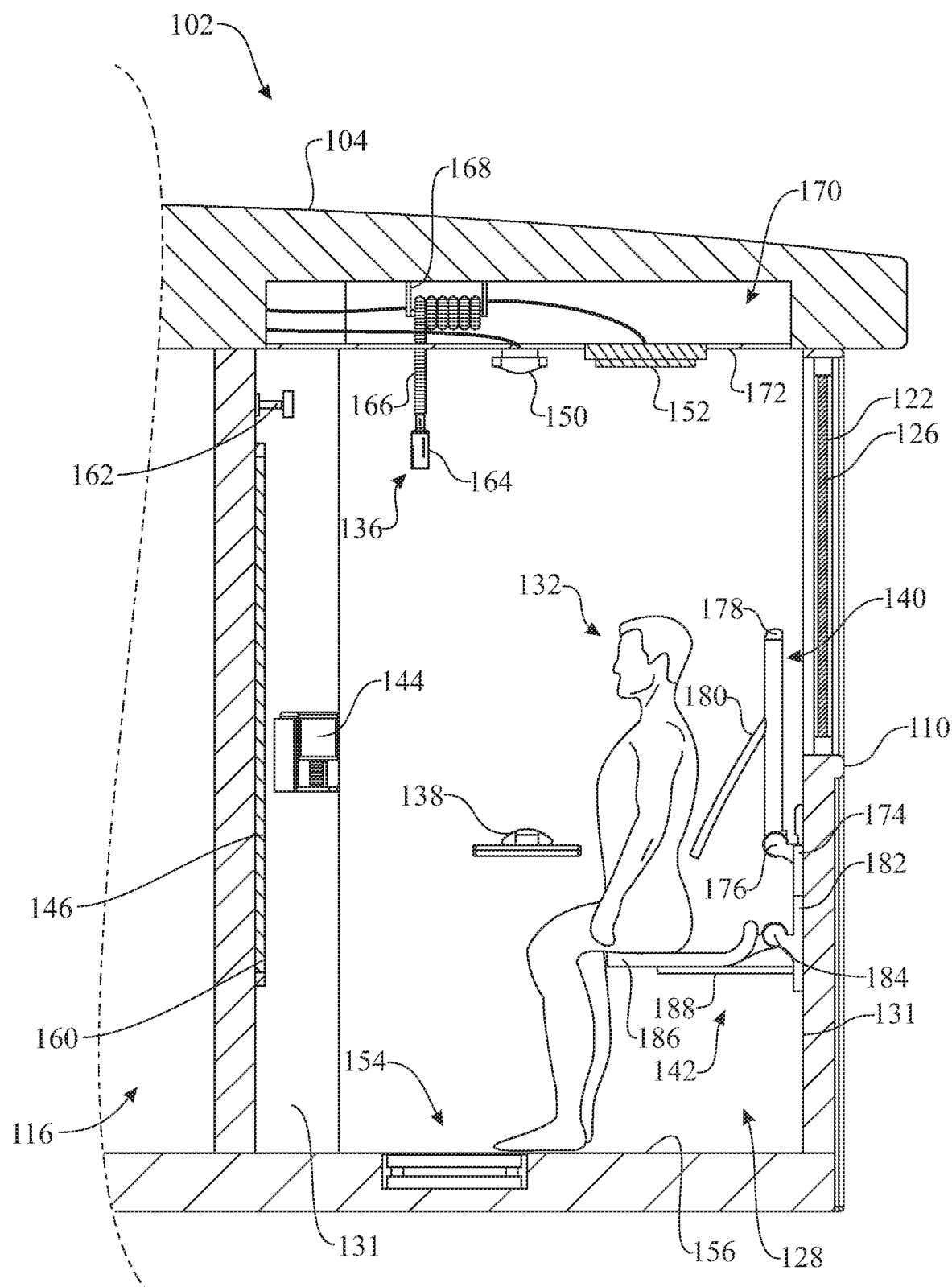
FIG. 10 presents a cross-sectional side elevation view of the medical service kiosk shown in FIG. 2, illustrating the patient sitting down talking with a physician on the interactive panel.
Figure 11:
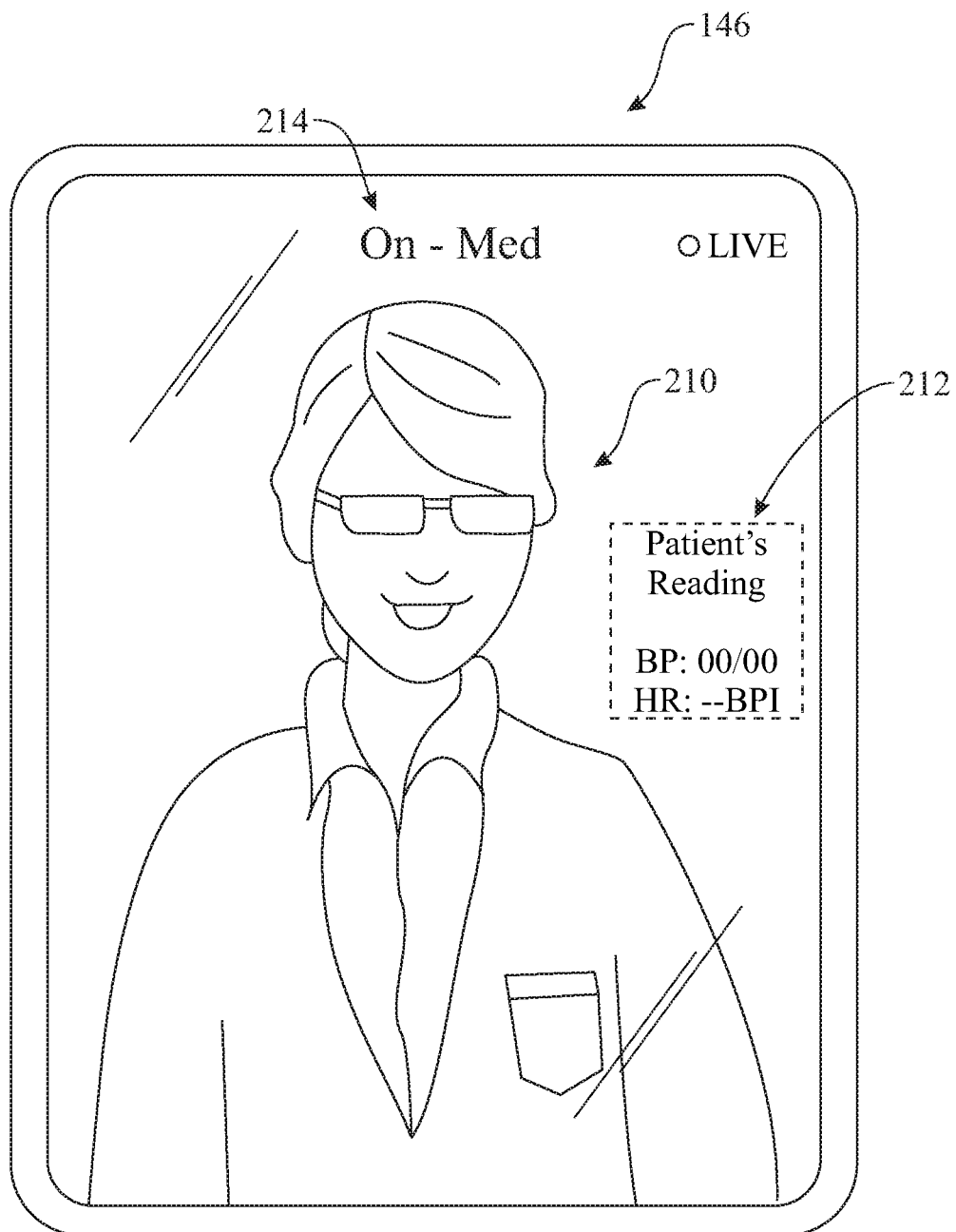
FIG. 11 presents one exemplary embodiment of how a physician would appear on the interactive panel included in the patient station.

Turning to FIGS. 7 and 11, each patient station 102 may include a user interactive display terminal 146 that is to be mounted on a wall surface 131 inside of the chamber 128 generally positioned below the capturing camera 162. The user interactive display terminal 146 includes a centralized processor communicable with the internal medical and non-medical equipment inside of the patient station (e.g., camera, diagnostic camera, biometric devices, medical storage unit, printer, etc.), and provides the means for a secure connection with the network 200, medical facility terminal 208, and cloud based system 300 hosting the medical session. The user interactive display terminal 146 is suitable for projecting (or displaying) a real-time image of the physician 210 (or medical professional) administering the exam remotely. As is clearly seen in FIG. 10, it is appreciated that the physician 210 be displayed to the patient 132 in such a way that the patient 132 receives the visual sensation that the physician 210 is virtually present in the room. It is also appreciated that the display of the user interactive display terminal 146 be configured to be adjusted manually or automatically to the height or preference of the patient 132, so that the physician 210 or health care professional performing the remote exam can see the patient 132 and what they are doing at all times. The medical services kiosk 100 is technologically equipped to the extent that the patient 132 is constantly receiving a live image of the physician 210 administering the exam, with the physician 210 having the ability to display on the screen (of the user interactive display terminal 146) any medical readings that are pertinent to the discussion of the diagnosis of the patient 132. For example, as shown and illustrated in FIG. 11, the physician 210 may be speaking to the patient while deciding to display a picture in picture (PIP) 212 at a respective visual corner on the display device of the user interactive display terminal 146 of the patient's 132 vital readings, sugar levels, blood levels, etc. The simulated screen image may also be configured to include a background image being displayed behind the physician 202 that may include, but is not limited to, the logo 214 or other indicator associated with the remote medical facility, physician, and/or insurance company covering the patient 132.

Returning to FIGS. 7, 9 and 10, the arm support mechanism 140 of the patient station 102 may comprise a wall mount 174 having a hinge connection 176 that is removably attachable to an arm rest 178 that includes a support arm

Figure 12:
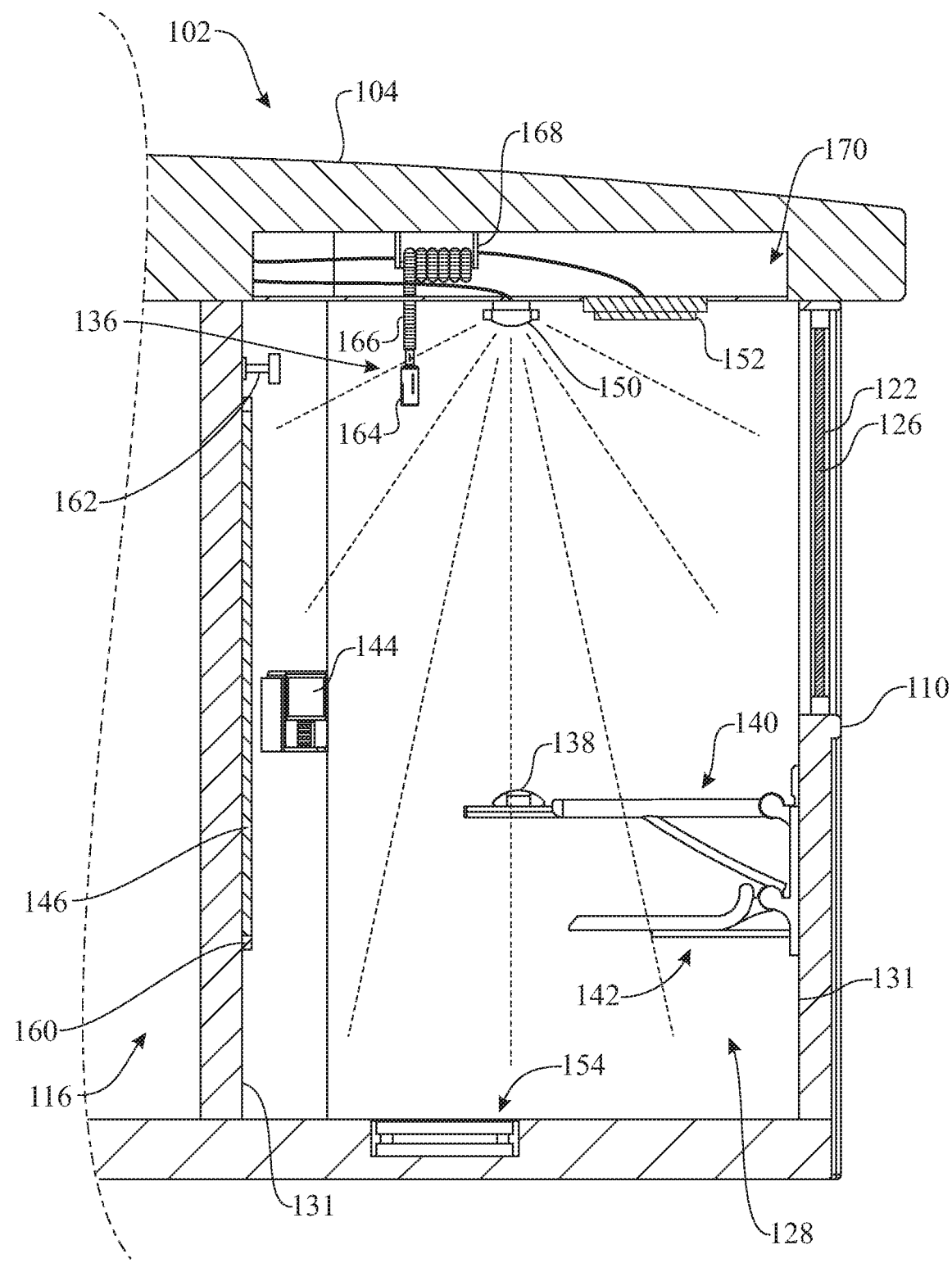
FIG. 12 presents a cross-sectional side elevation view of the medical service kiosk shown in FIG. 2, showing a cleaning mechanism being used to sanitize the room once the patient has left the patient station.

180. As illustrated, the wall mount 174 may be affixed to a wall surface 131, such that the arm rest 178 and support arm 180 can pivot about hinge 176 and be movable between an upward position (shown in FIG. 7) and downward position (shown in FIG. 12). The arm support mechanism 140 may be utilized to provide the patient 132 with an arm stabilizing platform that is necessary when performing certain diagnostic tests. For instance, when a physician 210 requests that the patient 132 take a blood pressure measurement, it is generally known that the arm placement of the patient must be in a bent position and remain still while the test is being performed. In that particular case, the patient 132 may decide to move the arm rest mechanism 140 from the upward position to the downward position and use the arm mechanism's arm rest 178 as a stabilizing platform to perform the test. Likewise, the arm support mechanism may be utilized for alternative tests that require the stabilization of the patient's arm (e.g., blood work, pulse and oxygen readings, etc.)

Figure 8:
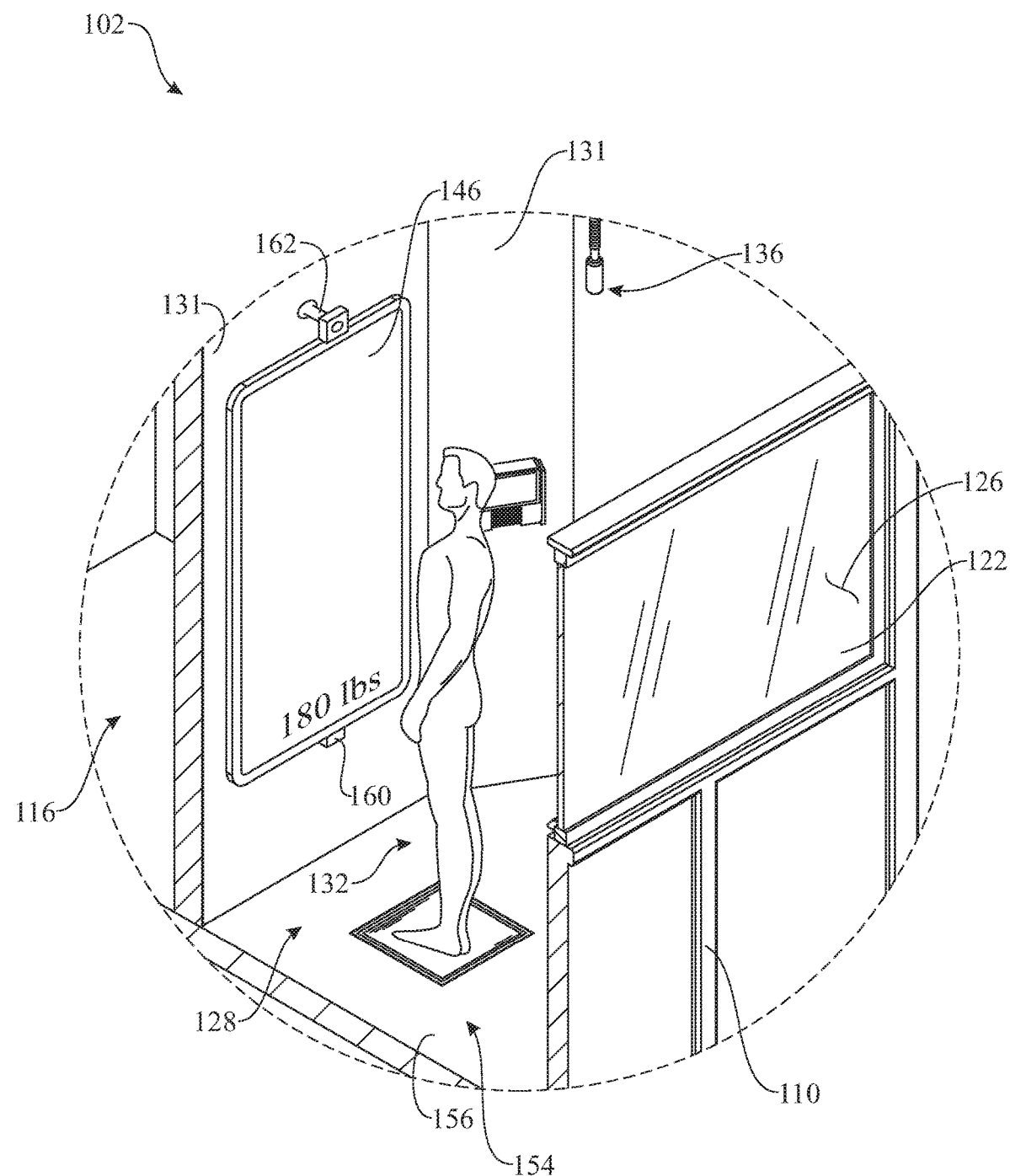
FIG. 8 presents a presents a cut-out view of the medical service kiosk shown in FIG. 2, illustrating a patient standing on top of a scale mechanism that's incorporated into the flooring system.
Figure 9:
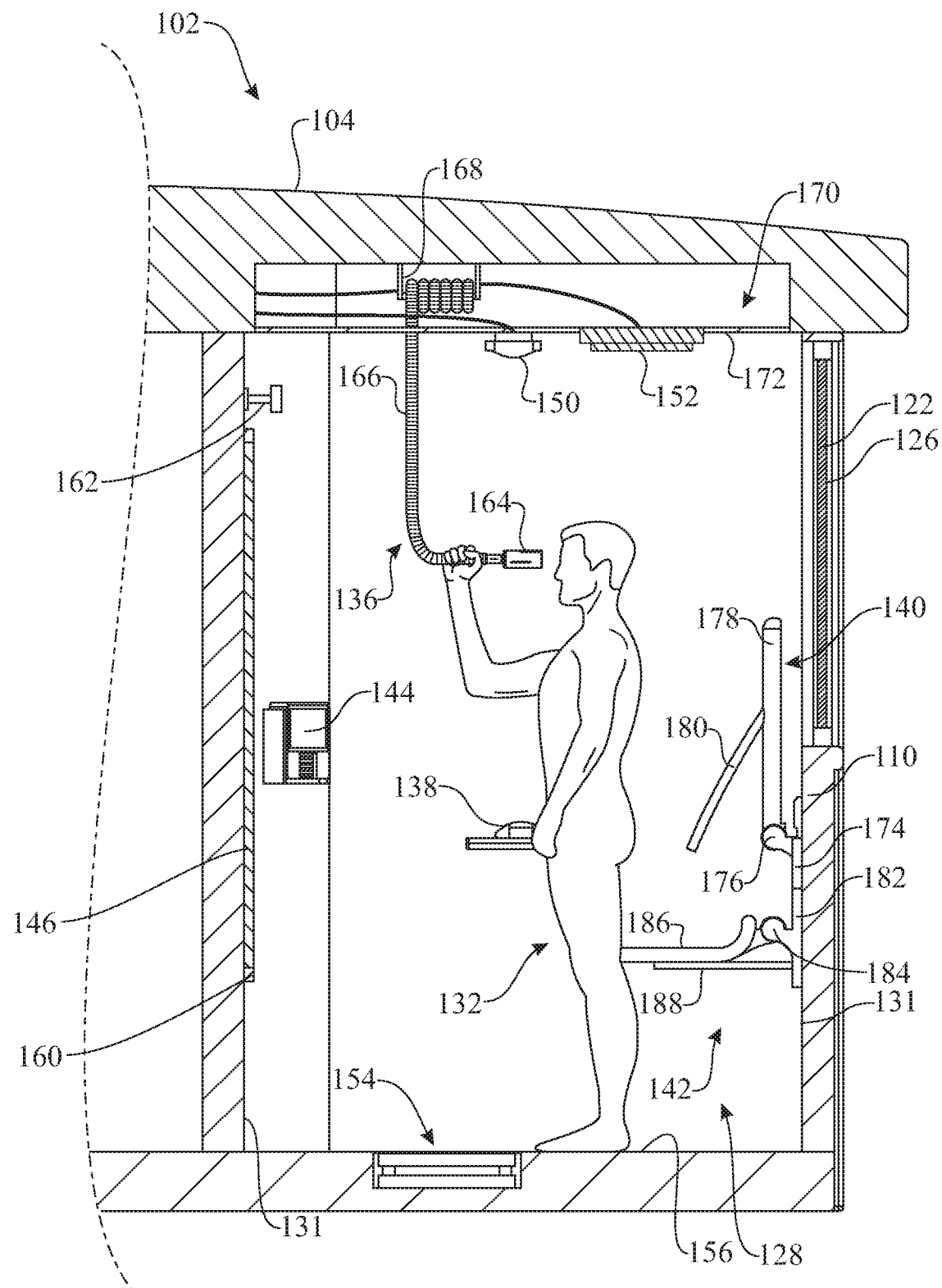
FIG. 9 presents a cross-sectional side elevation view of the medical service kiosk shown in FIG. 2, illustrating the use of the medical camera device included in each patient station.

Continuing with FIGS. 8 and 9, the seating mechanism 142 of the patient station 102 may generally comprise a wall mount 182 that includes a hinge connection 184, a seat 186, and a support member 188. In one exemplary form, wall mount 182 may be attached to a wall surface 131 proximate to the arm mechanism 140. Seat 186 may then be hingeably attached to hinge 184. The seat mechanism 142 is movable between an upward position (not shown) and a downward position (shown in FIG. 7), and is designed to withstand a heavy load of about 500 pounds. The seating mechanism 142 is contemplated to be positioned below and to a side of the arm support mechanism 140 that was described herein above. The relative position of the seat mechanism 140 and arm mechanism 140 is one that simulates a chair with an arm rest provided at an adequate height. Both the arm mechanism and seat mechanism may be height adjustable to account for patients of different sizes.

The operational use of the medical services kiosk, and more particularly, the patient station 102 that is provided in each medical service kiosk is now discussed with reference to FIGS. 1, and 6-12.

In operation, the patient 132 enters into one of the separated (i.e., private) interior chambers 128 of the patient station 102 through the entrance door 120. The patient 132 may then be able to initiate a session by interacting with the documentation receiving device 144 or user interactive display terminal 146. In one exemplary form, the initiation process may include the patient 132 entering a patient station 102 and interacting with the documentation receiving device 144 that is contemplated to be positioned at an opposite side of the patient station's entrance door 120, The documentation receiving device 144 may include a processing unit that is able to communicate with the centralized processing unit of the user interactive display terminal 146 that is communicable over the network 304 with the cloud based service 300 that is to host the medical session (FIG. 1), The patient 132 may initiate the session by providing payment or insurance information in the form of a card that is readable by the documentation receiving device 144 or providing information prompted by the user interactive display terminal 146 upon entry of the patient station 102. Once payment or the requirement to input information has been satisfied, the cloud based system 300 which is linked and communicates with the electronic device (i.e., terminal display 146) of the patient station begins the process of establishing a medical session with an available healthcare professional. The system begins by doing a search query to see which health care professional accessing a terminal 208 at a medical facility (or an electronic device 204 elsewhere) is available for a match. The process of facilitating or hosting a medical session executed by the cloud based system 300 may be carried out by a tangible computer-readable storage medium that holds machine-readable instructions executable by a logic machine (i.e. one or more processors or programmable control devices) to provide, implement, perform, and/or enact the described methods, processes and/or tasks. When such methods and processes are implemented, the state of the storage machine may be changed to hold different data. For example, the storage machine may include memory devices such as internal or external hard disk drives, CD, or DV') devices. The logic machine may execute machine-readable instructions via one or more physical information and/or logic processing devices. The logic machine may be configured to execute instructions to perform tasks for a computer program, and/or may include one or more processors to execute the machine-readable instructions. The computing system may include a display subsystem to display an application interface, or graphical user interface (GUI), or any visual element of the methods or processes described above.

To provide and ensure a secure, user-authorized access to a session, the physician or health care professional must go through an authentication process provided by the authentication server 302, which may include a software-based, and/or hardware-based authentication device, systems, or methods. Authentication may comprise a single-tier, two-tier, or multi-tier authentication protocol process. Examples of authentication protocols may include, but is not limited to, smart card technology, browser or digital certificates, hardware OTP tokens, software tokens, hardware security modules (HSM), or biometric authentication using one or more sensors for sensing fingerprints, hand geometry, iris or retinal patterns, or voice sampling or recognition. Other authentication protocols may include, IP security (IPSec) authentication methods, including the Kerberos protocol, private or public key certificates, or a simple pre-shared secret key, Challenge Handshake Authentication Protocol (CHAP), or the Extensible Authentication Protocol (EAP). Authentication based on single or multiple tier authentication system may include for example, use of a name/password, setting up answers to challenge questions, setting-up image recognition, or providing numerical or alphabetical information in a captcha text-entry box.

Once a patient has been matched with a physician and a bidirectional connection has been established, the patient 132 may be visually and auditorily prompted with additional introductory questions. For example, the patient 132 may be asked to provide and/or input additional information, such as medical history, if they are under any medications, or additional relevant information. In an alternative example, the information associated with the patient 132 may be linked and integrated from an outside data source by way of logging in to an account, which then may be accessible by both the patient and physician performing the remote medical assessment. As soon as the medical session has been established, the patient station's 102 privacy system 124 may be activated by the physician overseeing the medical session to lock door 130, and activate the privacy features on the glass surfaces 124, 126 of the door 130 and window panel 122 as described herein above. A message may be projected on the glass surface of the entrance door notifying other potential patients that the present patient station is in use.

Referring to FIGS. 7-10, the interior chamber 128 of the patient station 102 is configured for the patient 132 to sit in the patient seating mechanism 142 with their back aligned or supported by a wall surface 131 of the interior chamber 128, and able to use the arm support mechanism 140 provided, if necessary. The patient station 102 of the medical services system 100 may measure the weight of the patient 132 by requesting that the patient utilize the integrated scaling mechanism 154 provided therein, which is best shown in FIG. 8. The scaling mechanism 154 may include a calibrated scale, a plurality of measurement sensors, or any other means suitable for obtaining an accurate weight and/or height of the patient 132, and may be integrated with the remainder of the flooring 156 within the interior chamber 128. For instance, with respect to a height measurement, a height measurement device may be mounted to the ceiling of the interior chamber or a wall surface above a space that is to be occupied by the patient to measure the patient's height. The height measurement device may be connected to the electronic device included with the patient station.

As can be best understood by FIG. 9, the patient 132 is able to provide their biometrics and body vitals by applying, engaging, or otherwise using, the biometric/vitals measuring device(s) 138 provided inside of the patient station 102. In one non-limiting embodiment, the biometric/vitals measuring device 138 may comprise body sensors and blood pressure monitoring technology. The biometric/vial measuring device 138 may also include medical technology suitable for acquiring vital signs of the patient 132, such as, a telemetric monitor; EKG machine, and a pulse oximetry device. In one exemplary form, the biometric/vitals measuring device 138 may include an adjustable bracelet-like mechanism comprising a cavity suited for adjustable fitting to the arm of the patient 132 to obtain the blood pressure reading of the patient. In another example, the biometric/vital measuring device may include leads that are attachable to the patient to provide telemetry readings readable by the physician. As previously stated heretofore, the equipment inside of the patient station is communicable with the station's electronic device and configured to transfer data that is transferable over the network to the cloud based system 300 and remote network terminal 202 accessible by the physician 210 administering the exam remotely.

Additionally, the patient 132 under the supervision and guidance of a physician 202 may also use the retractable diagnostic camera device 136 suspended above the patient 132 or wall surface 131 to run a series of tests. For example, but not limited to, testing their pupillary light reflex, eyes; ears, both anterior and inferior surfaces of the patients nose, inspect their own mouth for oral mucosa, lesions, moisture cracking, etc. all under the careful guidance and watch of the physician.

As seen in FIG. 8, the head 164 of the retractable diagnostic camera device 136, which may be suspended above the standing patient 132, may be selectively grasped and pulled down by the patient 132. As the head 164 of the diagnostic camera 136 is pulled down, the camera cord 166 wrapped around the linear mechanism 168 suspended above the false ceiling 172 of the interior chamber 128 uncoils, providing the patient with sufficient cord length to easily point the head 164 of the diagnostic camera 136 wherever the patient is requested to do so by the physician administering the remote exam. After the patient 132 is done utilizing the diagnostic camera 136, it is appreciated that the linear mechanism includes a recoiling mechanism that when engaged the linear mechanism 168 recoils the portion of the camera cord 166 that was uncoiled when the patient pulled down the camera, thereby returning the diagnostic camera 136 back to its original position.

In summary, the patient 132 will be able to use the station's equipment to provide the remote examining physician 202 with any necessary data to render a medical diagnosis, or at the very least, allow the physician 202 to rule out medical conditions if a medical diagnosis can't be diagnosed by the physician.

Continuing in FIGS. 10 and 11, as previously stated the patient 132 will be able to have bidirectional communication with the physician 202 by way of the user interactive display terminal 146. The physician will be able to display relevant medical information on the user interaction panel's screen and talk to the patient 132 in real-time. As the session is coming to a close, the physician 202 may be able to dispense medication by way of the medical inventory storage space 116 included in the medical services kiosk 100. Alternatively, if the medication needed is not in-stock (or stored) by the inventory storage space 116, the physician will be able to put in an order remotely for the patient 132 to pick up their prescription at a nearby pharmacy; or print a prescription with by way of a printer that may be stored in the medical inventory storage space 116.

As shown in FIGS. 7, 9, 10 and 12, the privacy chamber or interior chamber 128 of the patient station 102 may include a purification or ultra-violet (UV) sanitation system 150. The ultra-violet sanitation system 150 can be disposed about the false ceiling 172 of the patient station 102. The UV sanitation system is generally controlled and powered by the PDU or control box 134. Similar to the description provided hereinabove with reference to the control box and privacy system, the UV sanitation system is governed by an executable set of instruction or commands provided by the control box 134. The UV sanitation system 150 may be commanded to activate by the physician overseeing the session as soon as the medical session has been terminated and the patient 132 has left the interior chamber 128. In one exemplary form, the physician may make an announcement that can be heard inside of the interior chamber before activating the UV sanitation system 150. Alternatively, the UV sanitation system can be programmed to run on a set schedule. For instance, the system may be programed to run for a pre-set amount of time every time it detects no movement within the chamber every 2 to about 4 hours during the day/night. Movement detection, in one exemplary form, may be verified by personnel viewing images being provided by the camera included in the interior chamber or through a motion sensor. The ultra-violet sanitation system 150 is designed to sterilize or sanitize the interior chamber 128 by neutralizing or killing organic and inorganic matter within the interior chamber 128 by way of ultraviolet lighting when the room is vacant and/or through the use of an ultrasound emitting device that neutralizes or kills organic and inorganic matter through ultrasound waves.

Figure 13:
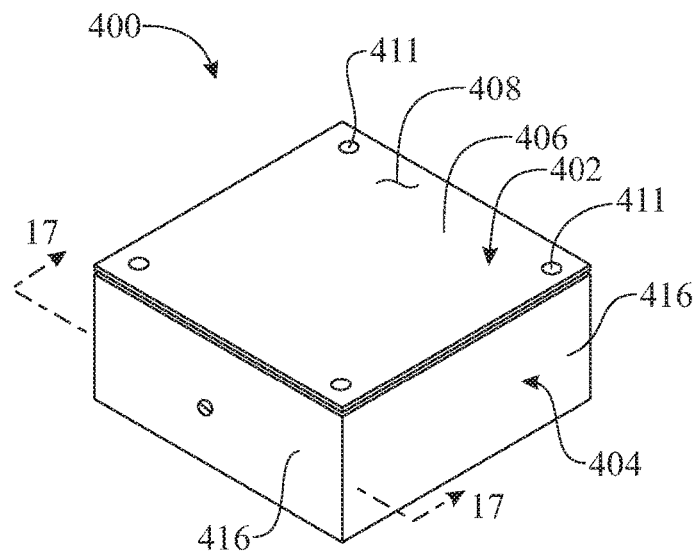
FIG. 13 presents a top isometric view of an exemplary embodiment of a weight scale assembly communicable with the centralized processor of the user interactive display terminal.
Figure 14:
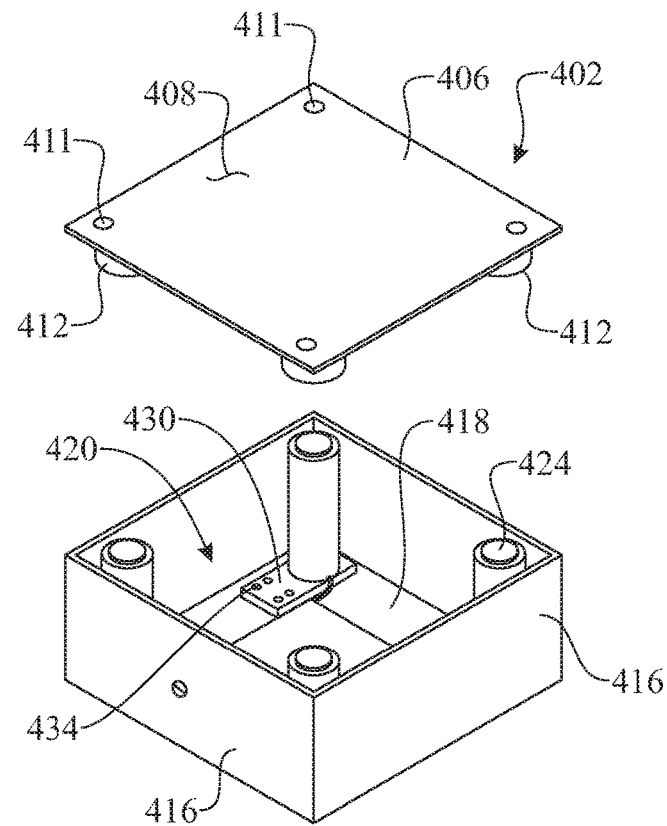
FIG. 14 presents a top isometric exploded view of the weight scale assembly of the present invention.
Figure 16:
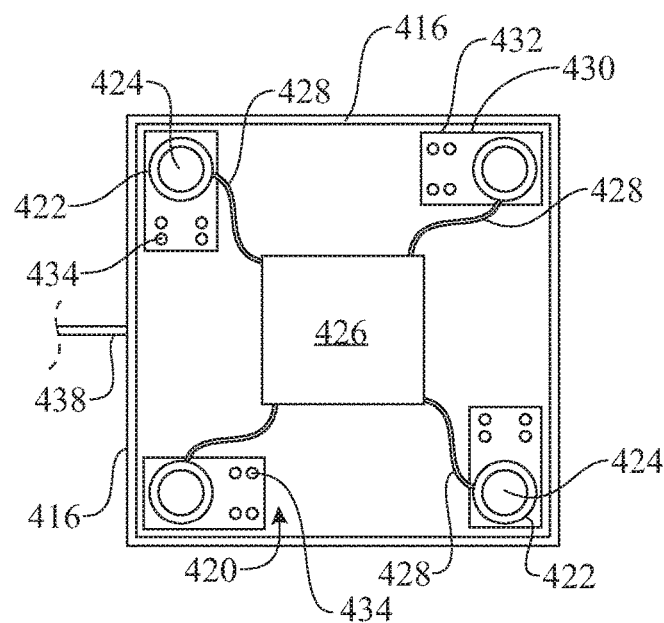
FIG. 16 presents a top side view of the weight scale assembly of the present invention.
Figure 17:
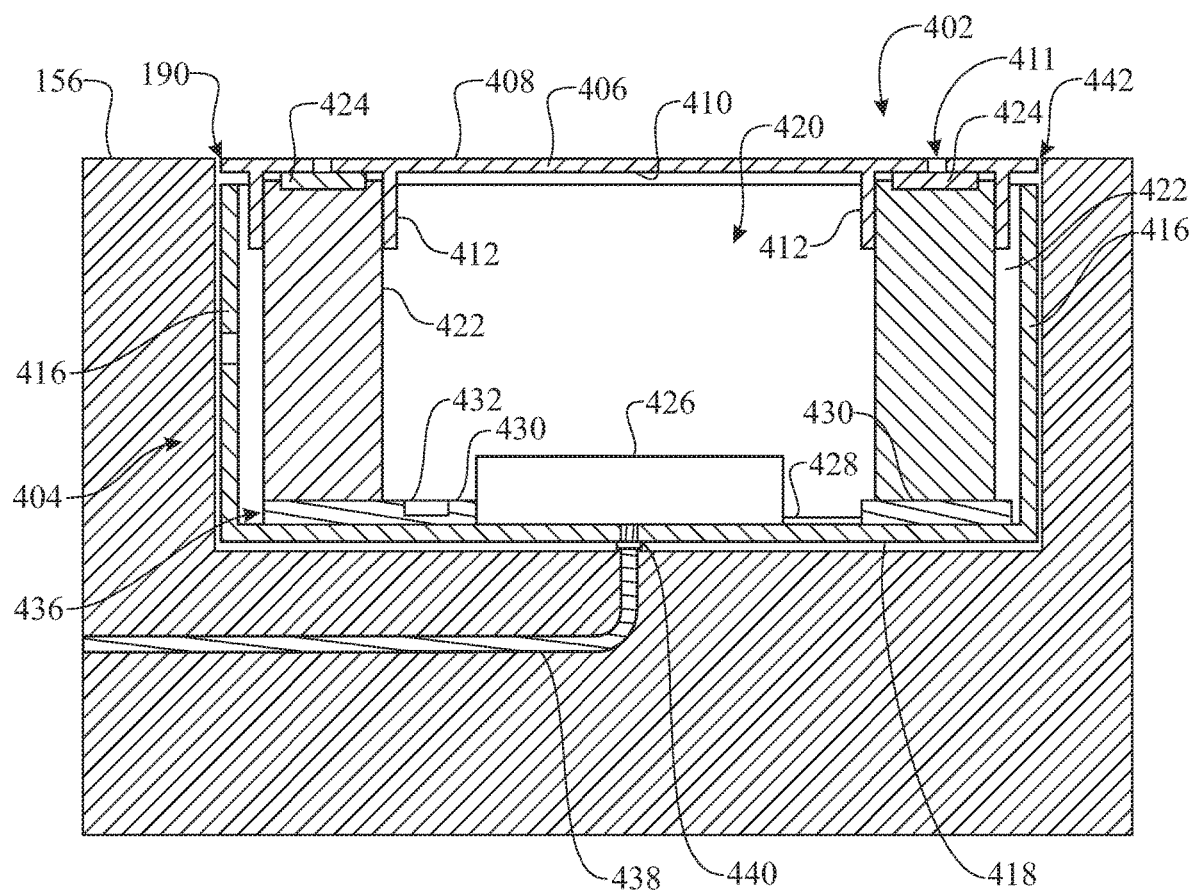
FIG. 17 presents a cross-sectional side elevation view of the weight scale assembly, the section taken along section plane 17-17 in FIG. 13.

Referring now to FIGS. 13, 14 and 17, as previously mentioned heretofore, the interior chamber 128 of the patient station 102 may include an integrated scaling mechanism 154 disposed about a cavity 190 in the flooring 156 of the interior chamber 128. The integrated scaling mechanism or the integrated weight scale assembly, now referenced as reference number 400 in FIGS. 13-17 for the sake of clarity, generally includes a top platform 402 and a housing 404. The platform 402 of the weight scale assembly 400 may generally comprise a singular planar wall 406 of a thickness having at least four sides (forming at least four corners), and provides a top end 408 and a bottom end 410. Disposed about the bottom end 410 of the weight scale assembly's platform 402 may be a plurality of retaining through-holes 411 adaptable to receiving a fastener (not shown). Alternatively, the platform 402 may include at least four projecting collars 412 with each of the collars 412 including an internal receiving hole 414. Each of the weight scale's collars 412 (or receiving holes 411) are generally positioned approximate to a respective corner on the platform 402. The holes 411 or collars 412 generally assist with the alignment and securement of the platform 402 of the weight scale assembly 400 when being placed over the housing 404.

Figure 15:
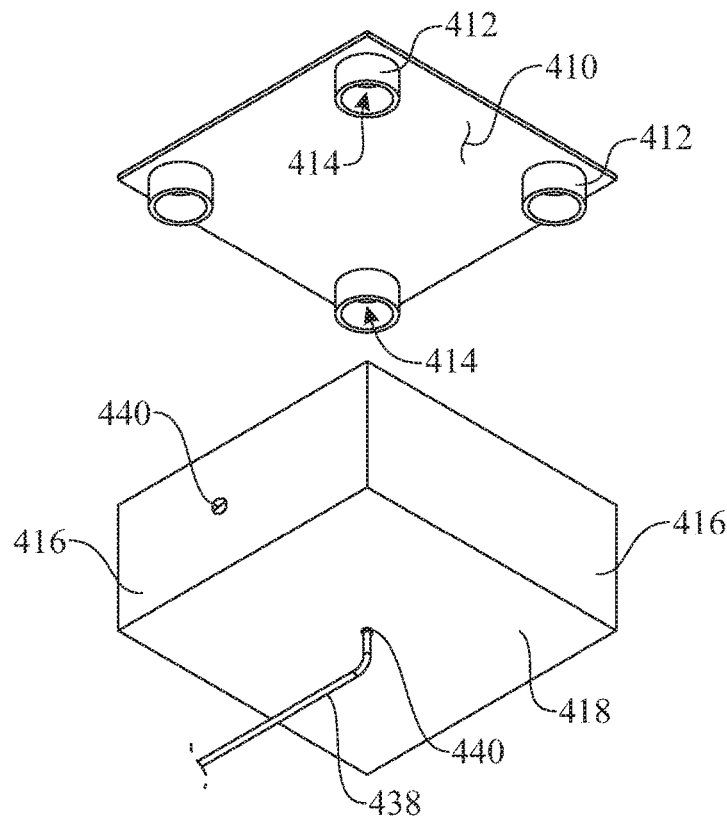
FIG. 15 presents a bottom isometric exploded view of the weight scale assembly of the present invention.

As shown in FIGS. 14 and 15, the weight scale assembly's housing 404 may generally comprise at least four contiguous upstanding side walls 416 affixed to a base 418 forming a hollow interior 420. Disposed about the four interior corners of the hollow interior 420 of the weight scale assembly 400 are at least four sensor blocks 422 each having a pressure block head 424. Each sensor block 422 may be affixed to a mounting bracket 430 that is selectively affixed to the base 418 of the weight scale assembly's housing 404 by way of fasteners (not shown). Each mounting bracket 430 may be arranged in a manner such that diagonally opposite mounting brackets are positioned in a mirror image of the other. All four sensor blocks 422 may be communicable with a (micro) processor 426 mounted to the base 418 of the housing 404 and disposed about the center of the housing's hollow interior 420, with each sensor block 422 being able to transfer readable data to the processor 426 by way of a communication cable 428.

Referring now to FIGS. 16 and 17, an illustrative assembly process of the weight scale assembly 400 is described.

The assembly process generally comprises coupling at least four mounting brackets 430 to the base 418 of the weight scale assembly's housing 404. The mounting brackets 430 are generally affixed to the base 418 at the respective corners formed by the at least four upstanding side walls 416 affixed to the housing's base 418. The mounting bracket 430 generally comprises a planar plate 432 having a plurality of fastener holes 434 on an end, and a mounting platform 436 for receiving the sensor block 422 on an opposite end. As is best illustrated in FIG. 16, adjacent mounting brackets 430 are positioned in a counter clockwise position with respect to the other. As previously stated, each mounting bracket may be securely affixed to the base 418 of the housing 404 by way of fasteners (not shown). A processor 426 may then be affixed to the base 418 of the housing 404 at a center point within the housing's hollow interior 420. Communication cables 428 from each sensor block 422 may then be connected to the processor 426 allowing the transfer of readable data by the processor produced by each sensor block 422. The processor 426 may also include a transmitting communication cable 438 that may be fed through an opening 440 either on the base 418 or an upstanding side wall 416 of the housing 404. The transmitting communication cable 438 generally transmits the readable data transferred to the processor 426 by the sensor block's communication cables 428 to the centralized processor of the electronic device or user interactive display terminal 146 of the interior chamber. The electronic device, which is communicable with the network 200 and cloud service system 300, may transmit readable data to the physician overseeing the medical session on the remote network terminal 208.

Once each of the communication cables 428 have been connected to the processor 426 and the transmitting communication cable 438 has been fed to the user interactive display terminal, the platform 402 of the weight scale assembly 400 is placed over the housing 404. The platform 402 covers the top end periphery of the housing's upstanding walls 416 and covers the housing's hollow interior 420. The platform may be affixed via a flat head fastener threaded through the plurality of retaining through-holes 411 provided on the platform 402 that line up with the pressure block head 424 and fastened thereto. The platform's collars 412 disposed about the bottom end 410 of the platform 402 may be concentrically aligned and placed over the pressure block head 424 of each respective sensor block 422, such that each pressure block head 424 is enveloped by the continuous side wall formed by each collar 412, and the top end surface of each pressure block 424 is in fluid contact with the bottom end 410 of the platform 402.

With reference to FIGS. 5 and 17, the flooring 156 of the interior chamber 128 of the patient station 102 includes a floor cavity 190. The floor cavity 190 may be provided in a square-shaped form, however, alternative shapes, such as a rectangular-shaped cavity may be provided. In one exemplary form, the cavity 190 is sized and shaped to be slightly larger than the size and shape of the weight scale assembly 400. During the installation process, the weight scale assembly 400 (which includes the platform 402, housing 404, pressure sensor blocks 422, pressure block heads 424, mounting brackets 430, processor 426 and communication cables 428, 440) is inserted into the cavity 190 with the weight scale assembly 400 fitting snugly inside of the cavity 190, and the platform 402 sitting flush with the surrounding flooring 156. In an alternative embodiment, the weight scale assembly may comprise of the pressure sensor blocks 422, pressure block heads, 424, mounting brackets 430, processor 426, and communication cables 428, 440 disposed about the interior cavity 190 of the patient station's flooring 156 and without a housing 404. Instead, platform 402 would be directly positioned over the sensor block heads 424 as described hereinabove to cover the cavity 190.

Referring now to FIGS. 5 and 17, an exemplary process of operational use of the weight scale assembly 400 after a medical session has been initiated by a patient is described.

Once the patient 132 has entered the patient station 102 and initiated a medical session with a physician (as described heretofore), the patient 132 may be asked by the medical professional overseeing the medical session or prompted by a pre-programed message displayed on the display device of the user interactive display terminal 146 to utilized the integrated weight scale assembly 400 to get a measurement reading. The measurement reading may be taken by the patient 132 standing on the weight scale's platform 402 and remaining there until instructed otherwise. When the patient 132 stands on the platform 402, the patient's mass pushes downwardly on the pressure block heads 424 of the sensor blocks 422 in contact with the bottom end 410 of the platform 402. The force being applied to each sensor block 442 is then transferred in the form of data to the (micro) processor 426 by way of the communication cables 428. The data received by the processor 426 is then communicated by the transmitting communication cable 438 to the centralized processor of the user interactive display terminal 146. The data transmitted is readable data that can be projected on the display device that is part of the user interactive display terminal 146, and/or be transmitted over the network to the network terminal 208 being accessed by the health care professional (e.g., a physician or nurse). It is contemplated that the weight scale assembly 400 be able to provide an accurate weight reading of up to about 500 pounds. It is also contemplated in one exemplary form that the weight scale assembly 400 be able to calculate the patient's body mass index (BMI), body fat percentage, muscle mass, body water percentage, bone mass and the like.

Since many modifications, variations, and changes in detail can be made to the described preferred embodiments of the invention, it is intended that all matters in the foregoing description and shown in the accompanying drawings be interpreted as illustrative and not in a limiting sense. Furthermore, it is understood that any of the features presented in the embodiments may be integrated into any of the other embodiments unless explicitly stated otherwise. The scope of the invention should be determined by the appended claims and their legal equivalents,

What is claimed is:

1. A method for using a weight scale assembly in a medical services kiosk that provides remote real time readings, said method including the steps of:
   (a) receiving a patient within a patient station, said patient station comprising:
      a privacy chamber formed by at least four upstanding side walls affixed to a flooring having a floor cavity and including at least one door, wherein said privacy chamber is provided for receiving a patient therein and allowing said patient to have a medical session over a network with an available remote health care professional;
      an electronic device, wherein said electronic device is electronically communicable over said network with a cloud based system and a remotely located network terminal accessible by said remote health care professional, wherein said medical session is hosted by said cloud based system;
      a purification system disposed within said privacy chamber;
      a weight scale assembly integratable with said floor cavity of said privacy chamber, comprising,
         a housing formed by at least four upstanding side walls affixed to a base defining a hollow interior,
         a platform of a planar configuration providing a top end and a bottom end, wherein said platform is securable to a top of said housing,
         a processor disposed within said hollow interior,
         a plurality of sensor blocks disposed within said hollow interior,
         a mounting bracket coupled to each one of said plurality of sensor blocks and affixed to said base of said housing,
         a communication cable connected to each one of said plurality of sensor blocks connecting said plurality of sensor blocks to said processor, and
         a transmitting communication cable, wherein said transmitting communication cable stems from said processor and is connected to said electronic device;
   (b) activating a search query to search for said health care professional available for said medical session;
   (c) establishing a connection between said electronic device and said remotely located network terminal over said network;
   (d) enabling bidirectional communication between said patient and said healthcare professional;
   (e) prompting said patient to step on said platform of said weight scale assembly;
   (f) establishing a measurement reading; and
   (g) terminating said medical session.

2. The method of claim 1, further comprising, after the step of (b), the step of matching said patient with said available remote health care professional for said medical session.

3. The method of claim 1, further comprising, after the step of (e), the step of transmitting data produced by said sensor blocks to said processor by way of said communication cable.

4. The method of claim 3, wherein the step of transmitting data from said sensor blocks to said processor includes the step of transmitting said data from said processor to said electronic device.

5. The method of claim 4, wherein said data transmitted from said processor to said electronic device is displayed on a display of said electronic device in readable form.

6. The method of claim 1, further comprising, after the step of (f), the step of displaying said measurement reading.

7. The method of claim 6, wherein said measurement reading is displayed on a display of said electronic device in readable form.

8. The method of claim 7, wherein said measurement reading being displayed on said display is in numerical form.

9. The method of claim 1, further comprising, after the step of (f), the step of transmitting over said network said measurement reading in the form of readable data to said remotely located network terminal.

10. The method of claim 1, wherein said network includes any one of a wired, a wireless, and an internet network.

11. The method of claim 1, wherein said privacy chamber further comprises a documentation receiving device.

12. The method of claim 1, further comprising, after the step of (b), step of requesting said patient to provide medical insurance information prior to the initiation of said medical session.

13. The method of claim 1, further comprising, after the step of (g), the step of activating said purification system after said patient has terminated said session and has left said privacy chamber.

14. The method of claim 11, wherein said purification system includes an ultraviolet light device.

15. The method of claim 1, wherein said measurement reading is a body weight reading.

16. The method of claim 1, wherein said measurement reading is a body mass index reading.

17. The method of claim 1, wherein said measurement reading is a body fat percentage reading.

18. The method of claim 1, wherein said measurement reading is a body water percentage reading.

19. A method for using a weight scale assembly in a medical services kiosk that provides remote real time readings, said method including the steps of:
   (a) receiving a patient within a patient station, said patient station comprising:
      a privacy chamber formed by at least four upstanding side walls affixed to a flooring having a floor cavity and including at least one door, wherein said privacy chamber is provided for receiving a patient therein and allowing said patient to have a medical session over a network with an available remote health care professional;
      an electronic device, wherein said electronic device is electronically communicable over said network with a cloud based system and a remotely located network terminal accessible by said remote health care professional, wherein said medical session is hosted by said cloud based system;
      a weight scale assembly integratable with said floor cavity of said privacy chamber, comprising,
         a housing formed by at least four upstanding side walls affixed to a base defining a hollow interior, a platform of a planar configuration having at least four sides providing a top end and a bottom end, wherein said platform is securable to a top of said housing, a processor disposed within said hollow interior, a plurality of sensor blocks disposed within said hollow interior, a mounting bracket coupled to each one of said plurality of sensor blocks and affixed to said base of said housing, a communication cable connected to each one of said plurality of sensor blocks connecting said plurality of sensor blocks to said processor, and a transmitting communication cable, wherein said transmitting communication cable stems from said processor and is connected to said electronic;

(b) activating a search query by said electronic device of said cloud based system for said health care professional available for said medical session;

(c) establishing a connection between said electronic device and said remotely located network terminal over said network, wherein said remotely located network terminal is accessible by a healthcare professional;

(d) enabling bi-directional communication between said patient and said healthcare professional;

(e) prompting said patient to step on said platform of said weight scale assembly;

(f) transmitting data produced by said sensor blocks to said processor by way of said communication cable;

(g) transmitting said data from said processor to said electronic device by way of said transmitting communication cable;

(h) establishing a measurement reading;

(i) displaying said measurement reading on a display of said electronic device, wherein said measurement reading being displayed is in numerical form; and (j) terminating said medical session.

20. A method for using a weight scale assembly in a medical services kiosk that provides remote real time readings, said method including the steps of:

(a) receiving a patient within a patient station, said patient station comprising:

a privacy chamber formed by at least four upstanding side walls affixed to a flooring having a floor cavity and including at least one door, wherein said privacy chamber is provided for receiving a patient therein and allowing said patient to have a medical session over a network with an available remote health care professional;

an electronic device, wherein said electronic device is electronically communicable over said network with a cloud based system and a remotely located network terminal accessible by said remote health care professional, wherein said medical session is hosted by said cloud based system;

a purification system disposed within said privacy chamber, wherein said purification system includes an ultraviolet light device;

a weight scale assembly integratable with said floor cavity of said privacy chamber, comprising, a housing formed by at least four upstanding side walls affixed to a base defining a hollow interior, a platform of a planar configuration having at least four sides providing a top end and a bottom end, wherein said platform is securable to a top of said housing, a processor disposed within said hollow interior, a plurality of sensor blocks disposed within said hollow interior, a mounting bracket coupled to each one of said plurality of sensor blocks and affixed to said base of said housing, a communication cable connected to each one of said plurality of sensor blocks connecting said plurality of sensor blocks to said processor, and a transmitting communication cable, wherein said transmitting communication cable stems from said processor and is connected to said electronic device;

(b) activating a search query by said electronic device of said cloud based system for said health care professional available for said medical session;

(c) matching said patient with said available remote health care professional for said medical session;

(d) establishing a connection between said electronic device and said remotely located network terminal over said network, wherein said remotely located network terminal is accessible by a healthcare professional;

(e) enabling bi-directional communication between said patient and said healthcare professional;

(f) prompting said patient to step on said platform of said weight scale assembly;

(g) transmitting data being produced by said sensor blocks to said processor by way of said communication cable;

(h) transmitting said data from said processor to said electronic device by way of said transmitting communication cable;

(i) establishing a measurement reading;

(j) displaying said measurement reading on a display device of said electronic device, wherein said measurement reading being displayed on said display device is a body weight reading presented in numerical form;

(k) terminating said medical session; and (l) activating said purification system after said patient has terminated said session and has left said privacy chamber.

* * * * *